US010729804B2

(12) United States Patent
Yliperttula et al.

(10) Patent No.: US 10,729,804 B2
(45) Date of Patent: Aug. 4, 2020

(54) NANOFIBRILLAR CELLULOSE COMPOSITION

(71) Applicant: UPM-KYMMENE CORPORATION, Helsinki (FI)

(72) Inventors: Marjo Yliperttula, Espoo (FI); Patrick Lauren, Espoo (FI); Petter Somersalo, Helsinki (FI); Yanru Lou, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 83 days.

(21) Appl. No.: 15/550,173

(22) PCT Filed: Feb. 10, 2016

(86) PCT No.: PCT/FI2016/050084
§ 371 (c)(1),
(2) Date: Aug. 10, 2017

(87) PCT Pub. No.: WO2016/128620
PCT Pub. Date: Aug. 18, 2016

(65) Prior Publication Data
US 2018/0021473 A1    Jan. 25, 2018

(30) Foreign Application Priority Data
Feb. 13, 2015   (FI) ................................. 20155101

(51) Int. Cl.
*C08L 5/04*      (2006.01)
*A61L 17/14*     (2006.01)
(Continued)

(52) U.S. Cl.
CPC ............. *A61L 17/145* (2013.01); *A61L 27/26* (2013.01); *A61L 27/34* (2013.01); *A61L 27/52* (2013.01);
(Continued)

(58) Field of Classification Search
None
See application file for complete search history.

(56) References Cited

U.S. PATENT DOCUMENTS 6,749,718 B2      6/2004  Takai et al.
2015/0306038 A1*  10/2015  Tran ..................... A61K 9/0095
                                                 424/93.45

FOREIGN PATENT DOCUMENTS

CN       103041438 B     10/2014
WO         9849202 A1    11/1998
(Continued)

OTHER PUBLICATIONS

Xiangning Shi et al. (pH-and electro-response characteristics of bacteria cellulose nanofiber/sodium alginate hybrid hydrogels for dual controlled drug delivery. (Year: 2014).*
(Continued)

*Primary Examiner* — Patricia L. Hailey
*Assistant Examiner* — Colette B Nguyen
(74) *Attorney, Agent, or Firm* — Nixon Peabody LLP

(57) ABSTRACT

The present invention relates to the use of nanofibrillar cellulose hydrogel in cell culture and medical applications. The invention relates to a composition comprising nanofibrillar cellulose, cross linkable polymer and at least one bioactive agent. The invention also provides methods for producing the composition and uses thereof. The present invention further relates to the use of said composition for manufacturing of a shaped matrix, the method of preparing said matrix, the matrix and the use of said matrix in various applications.

35 Claims, 13 Drawing Sheets

(51) Int. Cl.

| | | |
|---|---|---|
| A61L 27/26 | (2006.01) | |
| A61L 27/34 | (2006.01) | |
| A61L 27/52 | (2006.01) | |
| A61L 27/54 | (2006.01) | |
| A61L 27/58 | (2006.01) | |
| A61L 29/08 | (2006.01) | |
| A61L 29/14 | (2006.01) | |
| A61L 29/16 | (2006.01) | |
| A61L 31/04 | (2006.01) | |
| A61L 31/10 | (2006.01) | |
| A61L 31/14 | (2006.01) | |
| A61L 31/16 | (2006.01) | |
| C08B 1/00 | (2006.01) | |
| C08B 37/00 | (2006.01) | |
| C08L 1/02 | (2006.01) | |

(52) U.S. Cl.
CPC .............. *A61L 27/54* (2013.01); *A61L 27/58* (2013.01); *A61L 29/085* (2013.01); *A61L 29/145* (2013.01); *A61L 29/148* (2013.01); *A61L 29/16* (2013.01); *A61L 31/041* (2013.01); *A61L 31/10* (2013.01); *A61L 31/145* (2013.01); *A61L 31/148* (2013.01); *A61L 31/16* (2013.01); *C08B 1/003* (2013.01); *C08B 37/0084* (2013.01); *C08L 1/02* (2013.01)

(56) References Cited

FOREIGN PATENT DOCUMENTS

| WO | 2012107648 A1 | 8/2012 |
| WO | 2014/049204 A1 | 4/2014 |
| WO | 2014153210 A1 | 9/2014 |
| WO | 2014186430 A1 | 11/2014 |
| WO | 2016/100856 A1 | 6/2016 |

OTHER PUBLICATIONS

Catherine Kuo et al. (Ionically crosslinked alginate hydrogels as scaffolds for tissue engineering: Part 1. Structure, (Year: 2000).*
International Search Report and Written Opinion of International Searching Authority for Application No. PCT/FI2016/050084, dated Jun. 14, 2016 (18 pages).
Kanjanamosit, N. et al.; "Biosynthesis and characterization of bacteria cellulose-alginate film"; J. Applied Polymer Science, vol. 115, No. 3, pp. 1581-1588; Feb. 5, 2010; XP055261907; ISSN: 0021-8995 (8 pages).
Sirvio, J. et al.; "Biocomposite cellulose-alginate films: Promising packaging materials"; Food Chemistry, Elsevier Ltd., NL, vol. 151, pp. 343-351; Nov. 16, 2013; XP028668471; ISSN: 0308-8146 (9 pages).
Chiaoprakobkij, N. et al.; "Characterization and biocompatibility of bacterial cellulose/alginate composite sponges with human keratinocytes and gingival fibroblasts"; Carbohydrate Polymers, Jun. 2011, vol. 85, No. 3, pp. 548-553. Available from the Internet Nov. 15, 2011 <DOI: 10.1016/j.carbpol.2011.03.011> (7 pages).
Andersen, T. et al.; "Ionically Gelled Alginate Foams: Physical Properties Controlled by Operational and Macromolecular Parameters"; Amer. Chem. Soc., Biomacromolecules, vol. 13, pp. 3703-3710; Sep. 19, 2012. Available from the Internet: <dx.doi.org/10.1021/bm301194f> (8 pages).
Liu, K et al.; "Preparation of Microfibrillated Cellulose/Chitosan-Benzalkonium Chloride Biocomposite for Enhancing Antibacterium and Strength of Sodium Alginate Films"; J. Agricultural and Food Chemistry, Jun. 10, 2013; vol. 61, No. 26, pp. 6562-6567; <DOI: 10.1021/jf4010065> (7 pages).
Lin, N. et al.; "TEMPO-oxidized nanocellulose participating as crosslinking aid for alginate-based sponges"; ACS Applied Materials & Interfaces, Sep. 5, 2012; vol. 4, No. 9, pp. 4948-4959. Available from the Internet May 9, 2012 <DOI: 10.1021/am301325r> (13 pages).
Falanga, V.; "Stem Cells in Tissue Repair and Regeneration"; J. Investigative Dermatology, vol. 132, pp. 1538-1541; 2012; Available from the Internet: www.jidonline.org <doi:10.1038/jid.2012.77> (4 pages).
Kuo, C. et al.; "Ionically crosslinked alginate hydrogels as scaffolds for tissue engineering: Part 1. Structure, gelation rate and mechanical properties"; Elsevier Science Ltd.; Biomaterials, vol. 22, pp. 511-521; 2001 (11 pages).
Kutcharlapati, S. et al.; "Influence of Nano Cellulose Fibres on Portland Cement Matrix"; Metals Materials and Processes, 2008, vol. 20, No. 3, pp. 307-314; Meshap Science Publishers, Mumbai, India (8 pages).
Ma, Y. et al.; "Designing colon-specific delivery systems for anti-cancer drug-loaded nanoparticles: An evaluation of alginate carriers"; J. Biomed. Mater. Res. Part A, 2014:102A:3167-3176; Oct. 18, 2013. (10 pages).
Mansour, H. et al.; "Materials for Pharmaceutical Dosage Forms: Molecular Pharmaceutics and Controlled Release Drug Delivery Aspects"; Int. J. Mol. Sci., vol. 11, pp. 3298-3322; Sep. 15, 2010. Available from the Internet: <http://wwwmdpi.com/journal/ijms> doi:10.3390/ijms11093298 (25 pages).
Martínez, Á.H. et al.; "Novel bilayer bacterial nanocellulose scaffold supports neocartilage formation in vitro and in vivo"; Biomaterials, Jan. 12, 2015, vol. 44, pp. 122-133. Available from the Internet Dec. 1, 2015, <DOI: 10.1016/j.biomaterials.2014.12.025> (13 pages).
Park, M. et al.; "Nanocellulose-alginate hydrogel for cell encapsulation"; Carbohydrate Polymers, Feb. 2015, vol. 116, pp. 223-228. Available from the Internet Apr. 8, 2014 <DOI: 10.1016/j.carbpol.2014.07.059> (7 pages).
Shi, X. et al.; "pH- and electro-response characteristics of bacterial cellulose nanofiber/sodium alginate hybrid hydrogels for dual controlled drug delivery"; RSC Advances, Sep. 16, 2014; vol. 4, pp. 47056-47065; Available from the Internet Sep. 16, 2014. <DOI: 10.1039/C4RA09640A> (11 pages).
Yoo, S. M. et al.; "Fabrication of alginate fibers using a microporous membrane based molding technique"; Biochemical Engineering Journal, vol. 91, pp. 58-65, Jul. 12, 2014; (8 pages).
Wu, Y. et al.; "Mesenchymal Stem Cells Enhance Wound Healing Through Differentiation and Angiogenesis"; Stem Cells: Translational and Clinical Research (Jul. 5, 2007), vol. 25, pp. 2648-2659. Available from the Internet: <www.stemcells.com> (12 pages).
Finnish Patent and Registration Office, Search Report for Application No. 20155101, dated Oct. 12, 2015 (4 pages).
Office Action from Finnish Patent Application No. 20155101 dated Mar. 6, 2018.
Kajsa Markstedt, et al., "3D Bioprinting of Living Soft Tissues With Nanocellulose Ink", Biomaterials Research Centre's Annual Day, Nov. 18, 2014, "3D Printing in Biomaterials", Abstracts.
Yrr A. Mørch, et al., "Binding and leakage of barium in alginate microbeads", J Biomed Mater Res Part A 2012: 100A:2939-2947.
S.K. Bajpai, et al., "Investigation of swelling/degradation behaviour of alginate beads crosslinked with Ca2+ and Ba2+ ions", Reactive & Functional Polymers 59 (2004) 129-140.
S. Al-Musa, et al., "Evaluation of parameters involved in preparation and release of drug loaded in crosslinked matrices of alginate", Journal of Controlled Release 57 (1999) 223-232.
EP Communication from European Application No. 16 705 218.2 dated Sep. 5, 2018.

* cited by examiner

NANOFIBRILLAR CELLULOSE COMPOSITION

CROSS-REFERENCE TO RELATED APPLICATIONS

This application is a U.S. National Stage of International Application No. PCT/FI2016/050084, filed on Feb. 10, 2016, which claims priority to Finnish Patent No. 20155101, filed Feb. 13, 2015, the contents of each of which are incorporated herein by reference in their entireties.

FIELD OF THE INVENTION

The present invention relates generally to the use of nanofibrillar cellulose hydrogel in cell culture and medical applications such as tissue engineering. More particularly, the invention relates to a composition comprising nanofibrillar cellulose, cross linkable polymer and at least one bioactive agent. The invention also relates to a method for preparing a composition comprising nanofibrillar cellulose, cross-linkable polymer, and at least one bioactive agent. The present invention further relates to the use of said composition for manufacturing of a shaped matrix, the method of preparing said matrix and the matrix obtained. The invention also relates to the use of said matrix as a medicament and in treating diseases, such as Crohn's disease or defects of oral mucosa, such as ulcers. Furthermore, the present invention relates to a method of coating medical devices with said composition and uses thereof.

Applications of the present invention include nanofibrillar cellulose-cross-linkable polymer wire preparation and/or surgical suture coating with single cell type or co-cultures for post-surgical procedures and disease treatment.

BACKGROUND

Tissue engineering is a field wherein artificial tissues that can be used for medical applications are created in vivo, such as implantable organs, or in vitro, such as models for tissue functionality. Constructs which have been tissue engineered usually consist of a scaffold i.e. a porous matrix that has been seeded with cells. The properties of the matrix have a significant effect on the cell activity and functionality.

Nanofibrillar cellulose (NFC) has recently found applications in various areas, including biomedical and pharmaceutical applications as well as tissue engineering. In higher plants, cellulose is organized in morphologically complex structure consisting of β(1→4) D-glucopyranose chains. These chains are laterally bound by hydrogen bonds to form fibrils with a diameter in nanoscale, which are further organized in microfibril bundles. Furthermore, cellulose molecules are associated with other polysaccharides (hemicelluloses) and lignin in plant cell walls, resulting in even more complex morphologies. The cellulose nanoscale fibers can be released from the highly ordered structure by mechanical process and combined with other treatments, such as enzymatic pre-treatment. The cellulose nanoscale fibers can be used to form hydrogels which are a family of natural and synthetic polymers which can be used for cell culturing and tissue engineering.

An area in tissue engineering is the cell seeding process. Cells may be seeded either after or during fabrication. Additive manufacturing of biocompatible materials is a way to fabricate scaffolds for tissue engineering purposes. Additive manufacturing includes fabrication techniques that form 3D structures layer by layer. Some of said techniques are suitable for fabricating scaffolds from hydrogels. Ready-to-use alginate scaffold in well plates for cell culture, such as AlgiMatrix™ 3D Culture System (Gibco®), exists on the market.

Falange and Wu et al. (2012) disclose that stem cells have been used for wound healing and tissue repair. Sirviö et al. (2014) disclose biocomposite cellulose-alginate films produced using $Ca^{2+}$ crosslinking. The use of $Ca^{2+}$ only in crosslinking results in a stiff but fragile structure, wherein the cells are not able to move. Yoo et al. (2014) disclose fabrication of alginate fibers using microporous membrane based molding technique.

The existing cell culture compositions have problems such as the presence of starch which makes the composition too fragile. In addition, while some hydrogels can hold their shape after printing, they are often very soft and easily squashed when handled, which can ruin detailed structures.

Despite the ongoing research and development in the area of cell culturing and tissue engineering there is still a need for the development and use of generally acceptable methodologies in order to provide improved compositions and methods for cell culturing and tissue engineering. There is also a need for a method which enables transplanted cells to be adhered to the site they are delivered.

BRIEF DESCRIPTION OF THE INVENTION

Even though many advances have been made in the field of cell culturing and transplantation and tissue engineering, there is still a need to provide improved compositions and biomedical devices for use in various applications such as in therapy, diagnostics as well as surgical and post-surgical treatments.

The present inventors found surprisingly that when a cross-linkable polymer, for example alginate, is dissolved in the nanofibrillar cellulose hydrogel, and further when a bioactive agent, for example cell suspension, is mixed into this nanofibrillar cellulose hydrogel-cross-linkable polymer composition, a wire, which is useful in various biomedical applications, is obtained. The use of a cross-linkable polymer in the compositions enables crosslinking and thus stabilizing the hydrogel structure. For example the use of alginate including $Ca^{2+}$ and/or $Ba^{2+}$ is possible to enable crosslinking. Also the use of $Mg^{2+}$ in addition to or instead of $Ca^{2+}$ and/or $Ba^{2+}$ is possible.

The invention on hand relates to a composition comprising nanofibrillar cellulose, cross-linkable polymer, and at least one bioactive agent.

The composition of NFC and cross-linkable polymer such as alginate and containing also at least one bioactive agent, such as cells, can be printed. Nanofibrillar cellulose hydrogel-alginate, where alginate can also be an alginate-related crosslinkable polymer, is abbreviated herein as NFCA. The NFCA-bioactive agent composition of the present invention finds use in various medical applications. Biomedical devices, such as surgical sutures, can be coated with NFCA-bioactive agent compositions enabling combining surgical and post-surgical treatment.

A preferable feature of the NFCA-bioactive agent composition is that it is of non-human or non-animal origin. Another preferable feature is that NFCA-bioactive agent composition of the present invention is that wires are simple to prepare and wire structure is easily controlled.

An object of the present invention is to provide a novel composition comprising nanofibrillar cellulose, cross-linkable polymer, and at least one bioactive agent.

Another object of the invention is a method for preparing a composition comprising nanofibrillar cellulose, cross-linkable polymer, and at least one bioactive agent comprising the steps of combining in any order nanofibrillar cellulose, cross-linkable polymer and at least one bioactive agent.

It is known in the art that native NFC cannot be shaped, while anionically modified cellulose manufactured e.g. by TEMPO-mediated oxidation can be shaped and the shape is retained. Some hydrogels can hold their shape after printing, but they are often very soft and easily squashed when handled, which can ruin detailed structures. One aspect of the present invention is a composition that can be shaped and that the shape is retained. The cross-linking can be done at the same time as the composition is shaped.

The invention thus also relates to the use of the composition comprising nanofibrillar cellulose, cross-linkable polymer, and at least one bioactive agent in the manufacture of a shaped matrix, such as a wire, a cord, a tube, a mesh, a bead, a sheet, a web, a coating, an interlayer, or an impregnate.

One aspect of the present invention is a matrix comprising nanofibrillar cellulose, cross-linked polymer, and at least one bioactive agent.

The invention further relates to a method for preparing the matrix comprising nanofibrillar cellulose, cross-linked polymer, and at least one bioactive agent comprising the following steps:

combining in any order nanofibrillar cellulose, cross-linkable polymer, and at least one bioactive agent to obtain a composition; and cross-linking said cross-linkable polymer by exposing the composition to cross-linking conditions or chemicals.

The invention also relates to the use of the matrix comprising nanofibrillar cellulose, cross-linked polymer, and at least one bioactive agent in therapy, diagnostics, surgery or cosmetics. Use of the matrix as a suture coating and use of the matrix in biodegradable structures are also aspects of the invention.

A biomedical device comprising the matrix comprising nanofibrillar cellulose, cross-linked polymer, and at least one bioactive agent, preferably as a body or as at least one layer such as coating, is also one aspect of the present invention.

The invention relates also to a method for degrading the matrix or the biomedical device at least partially by treating the matrix or device with enzymes capable of degrading nanofibrillar cellulose. Such enzymes are for example cellulases, and/or enzymes capable of degrading the cross-linked polymer, such as cross-linked alginate with can be degraded with alginate lyases.

DEFINITIONS

Figure 1:
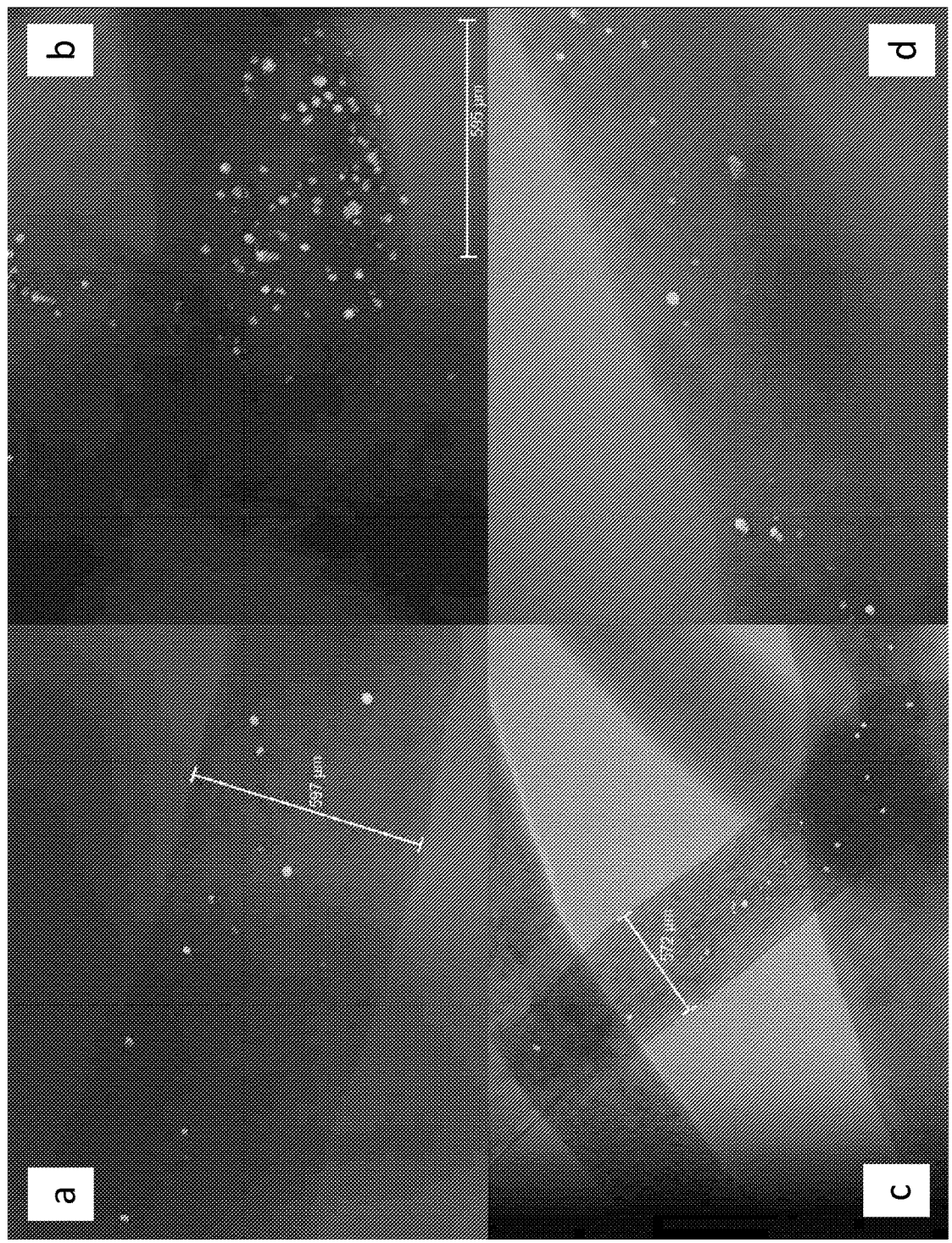
FIG. 1a depicts human hepatocellular carcinoma (HepG2) cells cultured inside NFC-Alginate wire. Live/Dead staining with fluorescent color FDA and PI shows live and dead cells, respectively. Image after 1 week of incubation. Scale bar 595 μm.
FIG. 1b depicts HepG2 cells inside NFC-Alginate wire. Live/Dead staining with FDA and PI shows live and dead cells, respectively. Image after 1 week of incubation. Scale bar 595 μm.
FIG. 1c depicts HepG2 cells inside NFC-Alginate wire. Live/Dead staining with FDA and PI. Image after 1 week of incubation. Scale bar 572 μm.
FIG. 1d depicts HepG2 cells inside NFC-Alginate wire. Live/Dead staining with FDA and PI. Image after 2 weeks of incubation. Scale bar 572 μm.

Unless otherwise specified, the terms, which are used in the specification and claims, have the meanings commonly used in the field of nanocellulose technology, as well as in the field of cell culture. Specifically, the following terms have the meanings indicated below.

As used herein, the term "nanofibrillar cellulose" or nanofibrillar cellulose or NFC is understood to encompass nanofibrillar structures released from cellulose pulp. The nomenclature relating to nanofibrillar celluloses is not uniform and there is an inconsistent use of terms in the literature. For example the following terms have been used as synonyms for nanofibrillar cellulose (NFC): cellulose nanofiber, nanofibril cellulose (CNF), nano-scale fibrillated cellulose, microfibrillar cellulose, cellulose microfibrils, microfibrillated cellulose (MFC), and fibril cellulose. The smallest cellulosic entities of cellulose pulp of plant origin, such as wood, include cellulose molecules, elementary fibrils, and microfibrils. Microfibril units are bundles of elementary fibrils caused by physically conditioned coalescence as a mechanism of reducing the free energy of the surfaces. Their diameters vary depending on the source. The term "nanofibrillar cellulose" or NFC refers to a collection of cellulose nanofibrils liberated from cellulose pulp, particularly from the microfibril units. Nanofibrils have typically high aspect ratio: the length exceeds one micrometer while the diameter is typically below 100 nm. The smallest nanofibrils are similar to the so-called elementary fibrils. The dimensions of the liberated nanofibrils or nanofibril bundles are dependent on raw material, any pretreatments and disintegration method. Intact, unfibrillated microfibril units may be present in the nanofibrillar cellulose but only in insignificant amounts.

Cellulose nanofibers described in this invention are not the same material as so called cellulose whiskers, which are also known as: cellulose nanowhiskers, cellulose nanocrystals, cellulose nanorods, rod-like cellulose microcrystals or cellulose nanowires. In some cases, similar terminology is used for both materials, for example by Kuthcarlapati et al. (Metals Materials and Processes 20(3):307-314, 2008) where the studied material was called "cellulose nanofiber" although they clearly referred to cellulose nanowhiskers. Typically these materials do not have amorphous segments along the fibrillar structure as cellulose nanofibers, which lead to more rigid structure. Cellulose whiskers are also shorter than cellulose nanofibers; typically the length is less than one micrometer.

The term "cross-linkable polymer" refers to a polymer which can be cross-linked as defined below. Cross-linkable polymer can be an anionic polymer, preferably cross-linkable by bivalent or trivalent cations. Cross-linkable polymer can be a biocompatible polymer. Cross-linkable polymer can be alginate and/or other compound behaving like alginate or alginate-related polysaccharides.

The term "cross-link" refers to a bond that links one polymer chain to another. The cross-linking can utilize divalent ions, such as $Ca^{2+}$ and $Ba^{2+}$ ions. Polymer chains can refer to synthetic polymers or natural polymers (such as proteins). When the term "cross-linking" is used in the synthetic polymer science field, it usually refers to the use of cross-links to promote a difference in the polymers' physical properties. When "crosslinking" is used in the biological field, it refers to the use of a probe to link proteins together to check for protein-protein interactions, as well as other creative cross-linking methodologies. Cross-linking is used in both synthetic polymer chemistry and in the biological sciences. Although the term is used to refer to the "linking of polymer chains" for both sciences, the extent of cross-linking and specificities of the crosslinking agents vary.

"Cross-links" in synthetic polymer chemistry include that when polymer chains are linked together by cross-links, they lose some of their ability to move as individual polymer chains. For example, a liquid polymer (where the chains are freely flowing) can be turned into a "solid" or "gel" by cross-linking the chains together. In polymer chemistry, when a synthetic polymer is said to be "cross-linked", it usually means that the entire bulk of the polymer has been exposed to the cross-linking method. The resulting modification of mechanical properties depends strongly on the cross-link density. Low cross-link densities decrease the viscosities of polymer melts. Intermediate cross-link densities transform gummy polymers into materials that have elastomeric properties and potentially high strengths. Very high cross-link densities can cause materials to become very rigid or glassy, such as phenol-formaldehyde materials.

"Cross-links" in the biological sciences include for example that proteins naturally present in the body can contain crosslinks generated by enzyme-catalyzed or spontaneous reactions. Such crosslinks are important in generating mechanically stable structures such as hair, skin and cartilage. Disulfide bond formation is one of the most common crosslinks, but isopeptide bond formation is also common. Proteins can also be cross-linked artificially using small-molecule crosslinkers. Compromised collagen in the cornea, a condition known as keratoconus, can be treated with clinical crosslinking.

Plants contain polysaccharides capable of forming hydrogels other than nanofibrillar cellulose. One of these is alginate, also called as algin or alginic acid. The term "alginate" refers here to an anionic linear polysaccharide found in species of brown algae. It is a block polymer consisting of β-1-4-linked mannuronic acid and guluronic acid. The length of the blocks varies depending of algae source. The monomers can appear in homopolymeric blocks of consecutive G-residues (G-blocks), consecutive M-residues (M-blocks) or alternating M and G-residues (MG-blocks). Alginate hydrogels can be ionically cross-linked for example with divalent ions such as calcium and barium ions: the positively charged ions bind to negatively charged guluronic acid blocks. G/M ratio and the molecular weight of alginate have an effect on the strength of an alginate hydrogel.

Alginate is known to be biocompatible, and is frequently used in tissue engineering (Kuo and Ma, 2001; Andersen et al., 2012). Alginate is also known to be shear-thinning (Ma et al., 2014), which is an important feature for the purpose of producing injectable composite materials. Alginate is available in filamentous, granular or powdered forms. Several grades of alginate are available.

The term "alginate-like crosslinkable polymer" refers to alginate and/or other compounds behaving like alginate and alginate-related polysaccharides.

Term "cross-linking conditions" refers to conditions where alginate or alginate-like cross-linkable polymer is cross-linked. For example when sodium alginate is put into a solution of calcium ions, the calcium ions replace the sodium ions in the polymer. Each calcium ion can attach to two of the polymer strands and cross-linking follows. Cross-linking techniques known in the art are such as immersion (IM) method and a pressure-assisted diffusion (PD) method. Cross-linking ions can be divalent or trivalent ions, such as $Fe^{3+}$, $Al^{3+}$, $Ca^{2+}$, $Ba^{2+}$ and $Sr^{2+}$.

Cross-linking can also be induced in materials that are normally thermoplastic through exposure to a radiation source, such as electron beam exposure, gamma-radiation, or UV light. Other types of cross-linked polyethylene are made by addition of peroxide during extruding (type A) or by addition of a cross-linking agent (e.g. vinylsilane) and a catalyst during extruding and then performing a post-extrusion curing.

The cross-linking efficiency is enhanced if pure water is used. Pure water has low conductivity, i.e. unknown ions are not present in water or their amount is minimal.

"Cross-linking chemicals" can be those well-known in the art, for example peroxide or vinylsilane and a catalyst.

The term "nanofibrillar cellulose-bioactive agent composition" or NFCA-bioactive agent composition" refers to at least one bioactive agent dissolved in the nanofibrillar cellulose hydrogel.

The term "nanofibrillar cellulose-alginate" or NFCA refers to alginate dissolved or dispersed in the nanofibrillar cellulose hydrogel.

The term "bioactive agent" refers to a substance that has or produces an effect on living tissue. Bioactive agent may have biological or pharmacological activity. In pharmacology biological activity or pharmacological activity describes the beneficial or adverse effects of a drug on living matter. Pharmacological/biological activity plays a crucial role since it suggests uses of the compounds in the medical applications.

Activity is generally dosage-dependent. Activity depends critically on fulfillment of the ADME (Absorption, Distribution, Metabolism, and Excretion) criteria. To be an effective drug, a compound not only must be active against a target, but also possess the appropriate ADME properties necessary to make it suitable for use as a drug.

In the present invention the bioactive agent is selected from the group consisting of cells, drugs, drug conjugates, anti-viral compounds, antibiotic compounds such as antifungal and antibacterial compounds, cell differentiating agents, wound repair agents, anti-proliferatives, analgesics, angiogenic agents, anti-angiogenic agents, anti-thrombotics, anti-clotting agents, clotting agents, adhesion-preventing agents, antipyretics, anaesthetics, anticonvulsants, antihistamines, anti-inflammatories, agents that act on the immune system, cardiovascular drugs, diagnostic agents, sympathomimetics, cholinomimetics, antimuscarinics, antispasmodics, hormones, growth factors, retinoids, cell adhesion factors, osteogenic factors, muscle relaxants, adrenergic antagonists, antineoplastics, immunogenic agents, immunosuppressors, immunostimulatory agents, neurotransmitters, digestive drugs, prodrugs, diuretics, steroids, lipids, narcotics, lipopolysaccharides, polysaccharides, peptides, polypeptides, proteins, carbohydrates, enzymes, viral particles, vectors, antibodies, antigens, therapeutic oligonucleotides, nucleic acids, and nucleic acid fragments, contrast agents for medical diagnostic imaging, and combinations thereof.

The term "cellulose pulp" refers to cellulose fibers, which are isolated from any plant based cellulose or lignocellulose raw material, using chemical, mechanical, thermo-mechanical, or chemi-thermo-mechanical pulping processes, for example kraft pulping, sulfate pulping, soda pulping, organosolv pulping. The cellulose pulp may be bleached using conventional bleaching processes.

The term "native cellulose pulp" or "native cellulose" refers here to any cellulose pulp, which has not been chemically modified after the pulping process and the optional bleaching process.

"Interpenetrated polymer network" (IPN) refers here to a polymer comprising two or more networks which are at least partially interlaced on a molecular scale but not covalently bonded to each other and cannot be separated unless chemical bonds are broken. IPN hydrogels can be classified in: (i) simultaneous IPN, when the precursors of both networks are mixed and the two networks are synthesized at the same time by independent, noninterfering routs such as chain and stepwise polymerization, and (ii) sequential IPN, typically performed by swelling of a single-network hydrogel into a solution containing the composition of monomer, initiator and activator, with or without a cross-linker. If a cross-linker is present, fully-IPN result, while in the absence of a cross-linker, a network having linear polymers embedded within the first network is formed (semi-IPN). IPN hydrogels known in the art are based on polysaccharides such as chitosan, alginate, starch, and other polysaccharides.

The term "matrix" in connection with a bioactive agents, such as cells or tissues or drugs, refers to a material consisting essentially of nanofibrillar cellulose, cross-linked polymer, and at least one bioactive agent, and which material is used for example for culturing, maintaining, transporting or delivering of cells or tissues, or for tissue engineering, or for delivering drugs, medicaments or other bioactive agents. The nanofibrillar cellulose may be in a form of a hydrogel or membrane. Said matrix may further contain various additives, such as special extra cellular matrix components, serum, growth factors, and proteins. The matrix may comprise semi-IPNs of nanofibrillar cellulose hydrogel and the cross-linked polymer. Matrix according to this invention can also comprise carriers for any bioactive agents. Cross-linked matrix contains alginate and/or other compounds behaving like alginate and alginate-related polysaccharides that have been exposed to the crosslinking method. Cross-linked matrix refers to polymer or molecules that can be reacted to form solid structure with pores.

The term "shaping" refers to shaping a composition, optionally in or on a secondary material. Shaping can be done by 3D-printing, spinning, spraying, dropping, spreading, coating or impregnation with concomitant or subsequent cross-linking, preferably shaping the composition directly into cross-linking conditions or chemical.

The term "shaped matrix" refers to matrix, which is in a shape such as a wire, a cord, a tube, a mesh, a bead, a sheet, a web, a coating, an interlayer, or an impregnate.

The term "hydrogel" in connection with nanofibrillar cellulose refers to a form where an aqueous dispersion of the nanofibrillar cellulose has a loss tangent less than 1.

Loss tangent values measure the ratio of loss modulus G" to storage modulus G'(G"/G').

The term "nanofibrillar cellulose hydrogel" refers here to an aqueous dispersion comprising plant-derived NFC.

Term "dispersion" in connection with nanofibrillar cellulose refers to a more dilute aqueous system not fulfilling the above requirement. NFC hydrogels are formed spontaneously without formation of covalent bonds, therefor their strength can be easily altered e.g. by dilution. NFC hydrogel has good suspending capacity. NFC hydrogel is so-called reversible or physical gel. The interactions in the network can be disrupted by application of stress, so NFC hydrogels have shear-thinning.

The term "wire" refers to wire-like thread prepared from NFCA that retains its hydrogel properties.

The term "body" refers here to matrix. A biomedical device can comprise the matrix as a planar or elongated body or bodies, preferably an implant, a dressing or a surgical suture.

The term "layer" refers to coating. With layer by layer technique NFCA can be layered with one cell type and then with another cell type resulting in multiple layers. This is how artificial organs such as liver (depending on selected cells) can be produced. NFCAs with different densities or thicknesses can be layered on a wire containing a drug. The cells are then layered on top of this cellulose layer.

The term "coating" refers to coating with NFCA with or without cells and/or with other bioactive agents. Medical devices can be coated with composition comprising NFC, cross-linkable polymer, and at least one bioactive agent. Surgical sutures can be coated for example with NFCA-HepG2. Also other cell types can be used for coating. In NFCA wire preparation and/or surgical suture coating single cell type or co-cultures can be used. The coating thickness may be varied.

The term "biomedical device" refers to an instrument, apparatus, implement, machine, implant, in vitro reagent, or related article including any component, part or accessory. Biomedical devices represent a wide variety of implements that are beneficial for human health and welfare. Biomedical devices may be used in the diagnosis of disease or other conditions, or in the cure, mitigation, treatment, or prevention of disease, in human or other animals. A biomedical device is intended to affect the structure or any function of the body of human or animals, and which does not achieve any of its primary intended purposes through chemical action within or on the body of man or other animals and which is not dependent upon being metabolized for the achievement of any of its primary intended purposes. Examples of biomedical devices are contact lenses, hip implants, pace makers, artificial heart valves, stents, catheters, breast implants, and surgical instruments. The biomedical device of the present invention may comprise a matrix comprising nanofibrillar cellulose, cross-linked polymer, and at least one bioactive agent. Said matrix may comprise IPNs of nanofibrillar cellulose hydrogel and the cross-linked polymer. The matrix of the invention especially comprises semi-IPNs. A biomedical device may comprise the matrix as a body or as at least one layer such as coating. A biomedical device of the present invention may comprise a planar or elongated element at least partially coated or embedded in the matrix, preferably a dressing or a surgical suture.

The term "biocompatible material" refers to, especially in surgery, to a synthetic or natural material used to replace part of a living system or to function in intimate contact with living tissue. Biocompatible material is also referred to as "biomaterial". Biocompatible materials are intended to interface with biological systems to evaluate, treat, augment or replace any tissue, organ or function of the body. Biomaterials are usually non-viable, but may also be viable. A biocompatible material is different from a biological material such as bone that is produced by a biological system. Artificial hips, vascular stents, artificial pacemakers, and catheters are all made from different biomaterials and comprise different medical devices. Different approaches to functionalization of biomaterials exist. Plasma processing has been successfully applied to chemically inert materials like polymers or silicon to graft various functional groups to the surface of the implant. Polyanhydrides are polymers successfully used as a drug delivery materials. The term "Biocompatible polymer" refers to a polymer which has characteristics of biocompatible material and is non-toxic.

The term "surgical suture" refers to a medical device used to hold body tissues together after an injury or surgery. Application generally involves using a needle with an attached length of thread. A number of different shapes, sizes, and thread materials have been developed. Surgical suture is commonly called stiches.

The term "co-culture" refers to a cell culture wherein one cell type grows inside the wire and another is attached to the surface. The co-culture enables different cell types to be utilized in a single treatment system.

The term "printing" refers to a process of producing NFCA structures and patterns as a printed material by means of 3D printing, laser assisted printing, extrusion, molding or electrospinning.

DETAILED DESCRIPTION OF THE INVENTION

The invention relates to a composition consisting of nanofibrillar cellulose hydrogel (NFC), cross-linkable polymer, such as alginate or alginate-like crosslinkable polymer, and at least one bioactive agent. It was surprisingly found that when cross-linkable polymer such as alginate or alginate-like crosslinkable polymer is added in solid form and let dissolve in the nanofibrillar cellulose hydrogel, nanofibrillar cellulose hydrogel-alginate (NFCA) is obtained. The alginate or alginate-like crosslinkable polymer in the composition enables $Ca^{2+}$ and $Ba^{2+}$ crosslinking thus stabilizing the hydrogel structure. Crosslinking occurs throughout the hydrogel, not only on the surface. NFCA wire cross-linked with $Ca^{2+}$ and $Ba^{2+}$ ions is strong enough to withstand light handling in a wet state. Also $Mg^{2+}$ can be used as an ion in crosslinking.

The NFC according to the invention is preferably plant-derived NFC. Preferable features of the plant-derived NFC hydrogel, which benefits the invention, is that it is inert;

non-toxic; non-pyrogenic; easy and inexpensive to manufacture. Moreover, the rheology of plant-derived NFC hydrogels show reversible gelation. At high stress levels, valid for injections, a fluid-like behavior is observed whereas at low stress level and quiescent conditions a step-wise transition to solid-like behavior. NFC hydrogel is a so-called physical or reversible gel, meaning that the network of hydrated and entangled cellulose nanofibrils in the NFC hydrogel is formed spontaneously without a need for further components such as cross-linkers. The interactions holding the networks together are reversible and can be disrupted e.g. by application of high stress. Upon removal of the stress the network is spontaneously formed again. In that regard the NFC hydrogel may be seen as a true one-component gel. The viscoelastic properties of the NFC hydrogels are similar to those of physiological extracellular matrixes (ECMs). Thus, the plant-derived NFC hydrogel is easy to handle and dispense, since it can be handled at room temperature, using automation; it is immediately ready for use; it is flexible and possible to modify with cells inside, i.e. to dilute or to add NFC; and thereto it does not contain protein residues. The plant-derived NFC hydrogel used is preferably transparent, light stable, electricity stable, and particularly native NFC is free of chemical residue. The cells within the hydrogel formed in cell culture media are possible to recover. The preferred NFC hydrogel is further highly stable, it may be stored at any desired temperature and it can be sterilized.

Nanofibrillar cellulose according to the invention can be nanofibrillar cellulose dispersion, preferably nanofibrillar cellulose hydrogel.

One aspect of the invention is a composition comprising nanofibrillar cellulose, cross-linkable polymer, and at least one bioactive agent.

Another aspect of the invention is a method for preparing a composition comprising nanofibrillar cellulose, cross-linkable polymer, and at least one bioactive agent said method comprising the steps of combining in any order nanofibrillar cellulose, cross-linkable polymer and at least one bioactive agent. In one embodiment the method comprises mixing at least one bioactive agent into nanofibrillar cellulose, optionally followed by incubation, and adding cross-linkable polymer to the obtained composition. In another embodiment the method comprises mixing cross-linkable polymer into nanofibrillar cellulose, and mixing at least one bioactive agent therein, optionally followed by incubation.

NFC is needed to soften the composition containing cross-linked polymer. NFC is preferably of native grade. NFC can also be of anionic grade. It is known that if cell growth composition is too stiff or too acidic, cells will not survive. Cationic NFC is not suitable material to be used to grow or maintain cells. The amount of nanofibrillar cellulose is usually small, such as from 0.1 to 10% (w/w), preferably from 1 to 5% (w/w), and more preferably from 1% to 2% (w/w). The amount can be such as 1%, 2%, 3%, 4%, 5%, 6%, 7%, 8%, 9%, or 10% (w/w). The amount of NFC is for example 1.35% (w/w).

In the present invention nanofibrillar cellulose is used as a dispersion or hydrogel.

Still another aspect of the invention is the use of the composition comprising nanofibrillar cellulose, cross-linkable polymer, and at least one bioactive agent in the manufacture of a matrix. This matrix thus comprises nanofibrillar cellulose, cross-linked polymer, and at least one bioactive agent. At least one bioactive agent may be encapsulated into the matrix. Matrix of the invention can be shaped matrix, such as a wire, a cord, a tube, a mesh, a bead, a sheet, a web, a coating, an interlayer, or an impregnate. Some hydrogels known in the art can hold their shape after printing, but they are often very soft and easily squashed when handled, which can ruin detailed structures. The matrix according to the present invention can be shaped. The shape of the matrix is retained.

The matrix according to the invention generally comprises semi-IPN of nanofibrillar cellulose and the cross-linked polymer. The matrix according to the invention can be in the form of a hydrogel.

The invention also discloses a method for preparing a matrix comprising nanofibrillar cellulose, cross-linked polymer, and at least one bioactive agent and a method for preparing the matrix wherein said matrix comprises semi-IPN of nanofibrillar cellulose hydrogel and the cross-linked polymer, said methods comprising the following steps:
   combining in any order nanofibrillar cellulose, cross-linkable polymer, and at least one bioactive agent to obtain a composition; and
   cross-linking said cross-linkable polymer by exposing the composition to cross-linking conditions or chemicals.

The method for preparing matrix comprising mixing at least one bioactive agent into nanofibrillar cellulose, can optionally be followed by incubation, and adding cross-linkable polymer to the composition, and cross-linking the polymer by exposing the composition to cross-linking conditions or chemicals. These steps are optionally followed by incubation, and adding cross-linkable polymer to the obtained composition. In one embodiment the method comprises mixing at least one bioactive agent into nanofibrillar cellulose, optionally followed by incubation, and adding cross-linkable polymer to the obtained composition. In another embodiment the method comprises mixing cross-linkable polymer into nanofibrillar cellulose, and mixing at least one bioactive agent therein, optionally followed by incubation.

The cross-linkable polymer is preferably a biocompatible polymer. According to another aspect of the invention the cross-linkable polymer is an anionic polymer, preferably cross-linkable by bivalent or trivalent cations. Preferably, the cross-linkable polymer is alginate or alginate-like cross-linkable polymer.

The amounts of NFC and cross-linkable polymer can be adjusted. The content of the nanofibrillar cellulose in the composition has an influence on the content of the cross-linkable polymer. The content of the cross-linkable polymer is determined and adjusted so that the characteristics of the final matrix is suitable for the desired purpose. Furthermore, in case alginate is used as a cross-linkable polymer G/M ratio and the molecular weight of alginate have an effect on the strength of an alginate hydrogel. The composition of NFC and cross-linkable polymer can be either exposed to cross-linking conditions or chemicals.

In a preferred embodiment of the present invention alginate is used as the cross-linkable polymer. Alginate can be used as powder form or dissolved in water solution and thereafter used as a solution.

In an embodiment of the invention sodium alginate powder is mixed and dissolved into NFC hydrogel, for example GrowDex®. The viscosity of the composition is adjusted. Addition of alginate increases viscosity. The content of the cross-linkable polymer, e.g. alginate in the final NFCA-cell composition may be from 0.5% to 40% (w/w), preferably from 5% to 10% (w/w), such as 1%, 2%, 3%, 4%, 5%, 6%, 7%, 8%, 9%, 10%, 11%, 12%, 13%, 14%, 15%, 16%, 17%, 18%, 19%, or 20% (w/w). The amount of cross-linkable polymer such as alginate is generally from 1% to 20% (w/w), preferably from 5% to 10% (w/w), and more preferably from 7% to 8% (w/w).

Alginate powder is preferably mixed with nanofibrillar cellulose and is allowed to dissolve and thereafter cells as are suspended in NFCA. In another embodiment alginate is mixed directly into existing NFC-cell cultures.

The presence of bivalent or trivalent cations is required for the cross-linking according to the invention. Crosslinking of alginate-like cross-linkable polymer is required to retain the desired shape or to retain the coating on a commercial surgical wire. The cross-linking cation is for example $Ba^{2+}$, $Ca^{2+}$ or $Mg^{2+}$ or any combination thereof. Preferably a bivalent cation is $Ca^{2+}$ or $Ba^{2+}$. More preferably, both $Ca^{2+}$ and $Ba^{2+}$ are used. Trivalent cations may be used in addition to or instead of divalent cations. The amount of $Ca^{2+}$, $Ba^{2+}$, $Mg^{2+}$, and/or a trivalent cation can be from 10 mM to 1000 mM, preferably from 50 mM to 500 mM.

The amount of $Ca^{2+}$ in the present invention can be e.g. 68 mM and the amount of $Ba^{2+}$ can be e.g. 20 mM $Ba^{2+}$. The ratio of $Ca^{2+}$ and $Ba^{2+}$ is for example 3:1. The ratio of those ions can also be for example 1:1, 2:1, 2.5:1, 2.6:1, 2.7:1, 2.8:1, 2.9:1, 3.1:1, 3.2:1, 3.3:1, 3.4:1, 3.5:1 or 4:1.

By this crosslinking it is possible to control the porosity and size of the pores in the wire. Furthermore, the length of the cross-linking time has an effect on the reaction.

Also a matrix comprising nanofibrillar cellulose, cross-linked polymer, and at least one bioactive agent is an aspect of the invention. The matrix can comprise semi-IPN of nanofibrillar cellulose hydrogel and the cross-linked polymer.

Preferably, the method for preparing matrix allows shaping the composition, optionally in or on a secondary material, preferably by 3D-printing, spinning, spraying, dropping, spreading, coating or impregnation with concomitant or subsequent cross-linking, preferably shaping the composition directly into cross-linking conditions or chemical.

In an embodiment of the present invention nanofibrillar cellulose hydrogel-alginate (NFCA) may be mixed with at least one bioactive agent such as cell suspension. Composition comprising NFCA and cell suspension is prepared for example in a syringe. Different cell types can be seeded into the NFCA composition before it is extruded through a nozzle or a needle into the crosslinking solution to prepare wire like structures. Different size nozzles or needles can be used to control wire thickness. The obtained wire is coilable and sufficiently strong for the purposes of suitable applications. Wires can be further coated to enable co-cultures (i.e. one cell type growing inside the wire and another attached on the surface). Patterns can be made by dispensing the composition on top of appropriate substrate.

In another embodiment the matrix comprises at least one bioactive agent encapsulated in the matrix.

In the cell growth composition of the present invention cells can be cultured at least 1 to 2 weeks. The cells can usually be cultured as long as needed in the cell growth composition of the present invention. For example cells within wire appear to be viable for 2 weeks. No signs of cell death were observed.

The composition of NFCA and cells can also be used for coating commercial surgical wires having hydrophobic surface and surprisingly this very hydrophilic material stays on the wire and the coated wire could be used in the sewing of soft tissues. The cells remain viable in the coating. Having cells in the wire or on/in the coating of wire is thought to facilitate better wound healing or other medical effects.

Possible applications include also oral mucosa repair (Hewitt; Alamoudi) or ulcer treatment (Gentileschi; Papa).

Commercial sutures can be coated with the composition of NFCA and cells. Preferably the composition or composition is prepared directly before use in order to keep cells alive.

Forming hollow wires having smooth muscle cells inside and endothelial cells on inner surface into a mesh those can possible create a blood-vessel like structures. Material porosity enables other materials and cells to interact within the constructed wire structures with biocomposites and materials.

NFCA can also be printed in other shapes than wire for other uses. NFCA product can have shape of wire but also other shapes are possible, such as net, asymmetric robe, balls with hollow inside, knitting with different wires with different cell types etc.

Any alginate can be used in the present invention. Alginate can be replaced with a cross-linkable polymer/compound which functions the same way as alginate. For example related polysaccharides can be used instead of alginate.

The following FDA approved drugs or drug products (Mansour et al., 2010) can be used in the present invention. These drugs can be used with biodegradable nanofibrillar cellulose and/or with biodegradable wire according to the invention.

Polyester-based synthetic polymers that can be used in the present invention can be for example PLGA (for IM, SC uses), Poloxamer (for oral, topical, IV ophthalmic, SC uses), Polyvinylpyrrolidone ethylcellulose (for oral use), Sodium pyrrolidone carboxylate (for topical use), Povidone (for oral, intra-articular, IM, Intrauterine, topical, SC, respiratory, opthalmic uses), PLA (for IM use), PEG (for oral, respiratory, topical, IM, IV, opthalmic uses), PVA (for auricular, IM, intraocular, topical uses), or KOLLIDON VA 64 (for oral use).

Natural-origin polymers that can be used in the present invention can be for example Starch (for oral, IV, IM, topical), Hyaluronate (for intra-articular, IM, intravitreal, topical uses), Human albumin (for IV, SC, Oral uses), Gelatin (for IM, SC, IV, oral topical uses), Alginic acid (for opthalmic and oral uses), or Collagen (for topical use).

Other suitable compounds that can be used in the present invention can be for example PDMS (polydimethylsiloxane), HPMC, microcrystal cellulose, polyvinylpyrrolidone (PVP) or latexes.

In an embodiment wherein cells are inside nanofibrillar cellulose hydrogel-alginate (NFCA) wire other types of cells can be added on the wire afterwards. The obtained wire can be used in medical applications. The wire can be rolled; it is not fragile.

Various medical devices can be coated with NFCA-cell composition such as threads, implants, wound treatment devices, different types of scaffolds and medical devices, porous membranes, filters and burns care cell membranes.

The invention also discloses the matrix as a suture coating. Any kind of surgical suture can be coated. Preferably the surgical suture is biodegradable.

Biodegradable surgical sutures can be coated with NFCA and cell/antibiotic compositions to prepare medical devices for post-surgical procedures such as Crohn's disease fistula treatment with mesenchymal adult stem cells or treatment of defects of oral mucosa with mesenchymal stem cells.

Cells can be embedded into the suture without the need of additional injections. In Crohn's disease as well as in oral mucosa defects the release of cells can be controlled as it can be induced with ingestion of cellulases or with cellulose enzymes already present within the surgical suture.

Biodegradable fiber structures coated with NFCA-cell compositions could be used for the production of thin hollow NFCA-cell hydrogel tubes by the degradation of the inner fiber. Tube structure (e.g. inner and outer diameters) can be controlled by varying the biodegradable fiber and coating thickness. NFCA can act as a scaffold for cell co-culture applications such as constructing blood vessels with the use of smooth muscle cells and endothelial cells.

A bioactive agent useful in the present invention can be for example a cell, a medicament, a drug, a drug conjugate or an antibody. Cells can be any cells. Any eukaryotic cell, such as animal cells, plant cells and fungal cells are within the scope of the present invention as well as prokaryotic cells. Prokaryotic cells comprise micro-organisms such as aerobic or anaerobic bacteria, viruses, or fungi such as yeast and molds. Even stem cells, such as non-human stem cells may be used in the present invention. Depending on the cell line, the experiments are carried out on 2D or 3D. Cells are growing in the 3D hydrogel or on the hydrogel. The matrix could be injectable hydrogel or sheet-like membrane optionally with appropriate surface topology. The composition comprising cellulose nanofibers or derivatives thereof can be used for immobilizing cells or enzymes.

In the present invention bioactive agent can be selected from the group consisting of cells, drugs, drug conjugates, anti-viral compounds, antibiotic compounds such as antifungal and antibacterial compounds, cell differentiating agents, wound repair agents, anti-proliferatives, analgesics, angiogenic agents, anti-angiogenic agents, anti-thrombotics, anti-clotting agents, clotting agents, adhesion-preventing agents, antipyretics, anaesthetics, anticonvulsants, antihistamines, anti-inflammatories, agents that act on the immune system, cardiovascular drugs, diagnostic agents, sympathomimetics, cholinomimetics, antimuscarinics, antispasmodics, hormones, growth factors, retinoids, cell adhesion factors, osteogenic factors, muscle relaxants, adrenergic antagonists, antineoplastics, immunogenic agents, immunosuppressors, immunostimulatory agents, neurotransmitters, digestive drugs, prodrugs, diuretics, steroids, lipids, narcotics, lipopolysaccharides, polysaccharides, peptides, polypeptides, proteins, carbohydrates, enzymes, viral particles, vectors, antibodies, antigens, therapeutic oligonucleotides, nucleic acids, and nucleic acid fragments, contrast agents for medical diagnostic imaging, and combinations thereof.

In the present invention the therapeutically useful cells comprise stem cells, undifferentiated cells, precursor cells as well as fully differentiated cells and combinations thereof, preferably selected from the group consisting of undifferentiated cells, precursor cells, fully differentiated cells, autologous cells, allogeneic cells, stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, cord blood cells, embryonic stem cells, induced pluripotent cells, placental cells, bone marrow derived cells, immune system cells, hematopoietic cells, dendritic cells, hair follicle cells, chondrocytes, cardiomyocytes, and hybridoma cells, and combinations thereof. Preferably fibroblasts, keratinocytes, endothelial cells, cardiomyocytes, and renal cells are used.

Stem cells, such as mesenchymal adult stem cells can be grown and maintained in the NFCA. If stem cells are used the NFC concentration must be low. NFC concentration can be under 1%.

Cells from harder tissues tolerate stiffer NFC, for example cells from kidney, heart, liver, vessel, or cancer cells, or neuronal cells.

A cell can be a cell which secretes proteins. A cell can be a therapeutic cell.

In one aspect of the invention the bioactive agent used in combination with NFCA or a wire coated with NFCA is a medicament, a drug, a drug conjugate or an antibody, such as monoclonal antibody.

The NFCA-cell composition of the present invention can be used in various medical applications. NFCA products can be used to facilitate e.g. wound healing so that the added cells provide tissue regrowth, or produce chemicals (such as growth factors, cytokines etc.) that diffuse easily through the matrix to surroundings to induce a desired effect (e.g. control or reducing of inflammation). Possible applications include also oral mucosa repair (Hewitt; Alamoudi) or ulcer treatment (Gentileschi; Papa).

A matrix according to the present invention can be used for example in therapy, surgery or diagnostics. The therapy may be for example the treating of Crohn's disease or oral mucosa defects, such as ulcers. The matrix can also be used in coating sutures. The matrix can be used in biodegradable structures.

The matrix can also be used in cosmetic applications, such as in the preparation of face masks, wrinkle creams, mascara bases, dry-skin protectants, and the like. Skin cosmetic composition can be designed for example in the forms of lotion, milky lotion, cream, gelated cosmetic and the like.

One problem with current methods for introducing cells into a desired place, such as wound, is that transplanted cells are not adhered to the site they are delivered. Delivering the cells on wire according to the present invention results in cells to be adhered to the desired site.

In an embodiment of the invention a product contains alginate, nanofibrillar cellulose and cells inside. Extrusion and crosslinking is carried out. The second cell type is added by coating e.g. using collagen or NFCA for coating.

Using e.g. layer by layer technique NFCA+one cell type and NFCA+another cell type artificial organs such as liver (depending on selected cells) can be produced. There is no need to liberate co-culture from matrix. Artificial liver could be used in real patient or for drug screening etc. Related to this the NFCA wire co-culture applications are also such as drug testing and analytics e.g. biomimetic NFCA scaffolds for hepatic tissue constructs with different hepatic cell lines to perform drug screening.

Drugs and drug conjugates can be used in the present invention instead of cells. The present invention enables controlled release drug delivery. For example a change of pH or temperature in tumor triggers the release of drug from the NFCA-cell composition.

In one embodiment of the invention NFCs with different densities or thicknesses are added on a wire containing a drug. The cells are then layered on top of this cellulose layer.

One object of the present invention is that at least two wires are weaved together. In an application of the present invention a wire containing a drug product can be weaved with another wire containing cells. In addition, a third wire with another type of cells can be weaved in this twine. A wire to be weaved can contain biodegradable and/or transparent NFC. Each of these wires can be of different densities enabling different pore sizes in cross-linking. An application of this kind of twine is for example diffusion controlled release of cells and/or drugs to the desired site.

An application of the present invention is to use NFCA-cell composition on heated nanoparticles, which are administered on the surface of the skin.

Another application of the present invention is to use NFCA-cell composition on medical device. A biomedical device comprising the matrix according to the invention, preferably as a body or as at least one layer such as a coating. The biomedical device may also comprise a planar or elongated element at least partially coated or embedded in the matrix, preferably a dressing or a surgical suture. One object of the invention is also a biomedical device comprising the matrix as a planar or elongated body or bodies, preferably an implant, a dressing or a surgical suture.

The dosage of NFCA for treatment application has to be determined during the patient care and is also dependent of the state of the disease and patient.

By using NFCA-based materials produced by the methods according to the invention, surgical and post-surgical treatment can be combined. There will be no rejection since same material is used in both treatment procedures.

The composition of NFCA and cells can be printed. A skilled person in the art is able to choose a suitable printing technique, such as silk screen printing, extrusion or casting. The benefit of silk screen printing is that it is shear thinning, cells can permeate the wire and therefore do not suffer from the process.

According to one aspect of the invention, after surgery the bioactive ingredients are released from the wire e.g. along the blood vessels or inside the tissues to be prepared. Wire provides a controlled release.

According to one aspect of the invention alginate can be removed from NFCA using alginate lyase. The removal is required if the cells are wanted to be released.

By treating the matrix or device with enzymes capable of degrading nanofibrillar cellulose, such as with cellulases, the matrix or device can be degraded at least partly. The viscosity of matrix can be controlled with adjusting the amount of enzymes. The removal of NFC can be carried out for example with enzyme compositions comprising all necessary enzymes for total degradation of cellulose molecules. The degradation product, glucose, is generally non-toxic to cells and can be thus utilized as a nutrient in cell culturing. In case enzymatic hydrolysis, such as a cellulase, is used in breaking the NFC hydrogel, the enzyme may be inactivated or removed from the system wherein hydrogel is utilized. A skilled person is readily able to select any appropriate method to inactivate or remove the enzyme. Examples of suitable methods include inactivation by inhibitors or neutralizing antibodies, and removal of the cellulase by washing, filtration, affinity purification, or any other method which is suitable for the selected application. Removal of the enzyme may be required in certain downstream applications. If complete degradation of matrix is desired it can be treated also with enzymes capable of degrading the cross-linked polymer, such as cross-linked alginate with alginate lyases. Matrix comprising alginate as described herein can be degraded using alginate lyase, which is a bacterial enzyme that interacts with the alginate backbone. Such specific interaction can be important, because rapid gel degradation is preferable for example for releasing cells captured by the functionalized coatings or layers. Alginate lyase can degrade alginate by cleaving the glycosidic bond through a β-elimination reaction, generating oligomer with 4-deoxy-L-erythro-hex-4-enepyranosyluronate at the non-reducing end.

Thus, according to the present invention, the method for degrading the matrix or the biomedical device at least partially is characterized by treating the matrix or device with enzymes capable of degrading nanofibrillar cellulose, such as with cellulases, and/or with enzymes capable of degrading the cross-linked polymer, such as cross-linked alginate with alginate lyases.

The present description also comprises a method of treating a disease or disorder comprising the steps of providing a composition comprising NFCA wire and a bioactive agent.

EXAMPLES

Example 1

Preparation of NFC-Alginate Wire Including HepG2 Cells

Sodium alginate powder (Sigma Aldrich) was added into the stock NFC hydrogel (1.47% NFC, GrowDex®, UPM-Kymmene Corporation, Finland). After mixing the sodium alginate was allowed to dissolve. The NFCA composition contained 8% (w/w) sodium alginate and 1.35% NFC (w/w).

Rheological measurements were done with an Anton Paar-Physica MCR 301 Rheometer (Anton Paar, GmbH, Germany) using a plate-plate geometry. Diameter of the plate was 25 mm and the gap between the plates was set to be 1 mm. Experiments were done at 25° C. The effect of frequency on storage and loss moduli was measured with a frequency sweep (0.1-100 Hz at 0.1% strain), and the effect of shear stress on viscosity were measured with shear stress sweep (0.01-500 Pa at the frequency of 1 Hz). Sample materials included stock NFC hydrogel and compositions containing 7, 8 or 9% (w/w) sodium alginate. Both treated and un-treated samples were tested. Also, samples containing cells and culture media were tested to see if they have any effect on the properties of the gels. The cell concentration of the cell-containing sample was approximately 850 000 cells/ml. The total sample volume for each individual sample was approximately 3 ml.

Human hepatocellular carcinoma HepG2 (ATCC® HB-8065™) and human adenocarcinoma SK-HEP-1 cells (ATCC® HTB-52™) were cultured in high glucose Dulbecco's modified Eagle's medium (Gibco®, Scotland) supplemented with 10% fetal bovine serum, 100 U/ml penicillin, 100 μg/ml streptomycin, 2 mM L-glutamine and 100 mM sodium pyruvate. Cell cultures were maintained in 37° C. and 5% $CO_2$ until 70-80% confluence before detachment and preparation of cell suspensions.

HepG2 cells were detached, centrifuged and suspended and mixed into the NFCA composition. The NFCA-HepG2 composition contained 1043 cells/μl. Final concentrations of the sodium alginate and NFC were 7% and 1.17% (w/w) respectively.

The NFCA-HepG2 composition was dispensed using a syringe with a needle of size 22G. Crosslinking was performed by extruding the composition into a 68 mM $Ca^{2+}$ solution and incubated for 3 minutes. The produced wire was transferred into a 20 mM $Ba^{2+}$ solution for additional 5 minutes. $Ca^{2+}$ and $Ba^{2+}$ crosslinking stabilized the hydrogel-wire structure to withstand handling in its wet state. Afterwards the wire was transferred into cell culture medium, which was Dulbecco' Eagle's medium 41966 supplemented with 10% fetal bovine serum, 100 U/ml penicillin and 100 μg/ml streptomycin. Incubation was carried out at 37° C. and in 5% $CO_2$.

NFC-alginate wires including HepG2 cells are presented in FIGS. 1a, 1b and 2a after 1 week of incubation and in FIG. 2b after 2 weeks of incubation.

NFC-Hydrogel and Salt-Treatment

NFC-hydrogel (GrowDex™, UPM-Kymmene Corporation, Finland) with a starting concentration of 1.47% was used in the experiments. Organic polymer Z, which refers herein to alginate, was added to this stock NFC-hydrogel in various concentrations (7, 8 or 9% (w/w)). Some gel samples were treated with inorganic salts in order to induce solidification. Inorganic salts used herein are those of Calcium or Barium. Cells and cell culture media were added to some samples. The contents and concentrations of studied samples are shown in Table 1.

TABLE 1

Hydrogel samples used in the experiments.

| Sample name | NFC content (w/w) | Z content (w/w) | Media content (v/v) | Salt-treatment |
|---|---|---|---|---|
| NFC | 1.47% | 0% | 0% | No |
| NFC + Z7% | 1.36% | 7% | 0% | No |
| NFC + Z8% | 1.35% | 8% | 0% | No |
| NFC + Z9% | 1.34% | 9% | 0% | No |
| NFC + Z7% X | 1.36% | 7% | 0% | Yes |
| NFC + Z8% X | 1.35% | 8% | 0% | Yes |
| NFC + Z9% X | 1.34% | 9% | 0% | Yes |
| NFC + Z8% + C | 1.12% | 7% | 15% | No |
| NFC + Z8% + M | 1.12% | 7% | 15% | No |

'Z' followed by a percentage refers to the content of polymer Z (alginate) in the sample.
'X' refers to treatment with inorganic salts.
'C' refers to culture media with cells.
'M' refers to culture media without cells.

Example 2

Coating of NFCA Wire

The produced wire structures were further coated to enable co-cultures (i.e. one cell type growing inside the wire and another attached to the surface). Co-culture applications can be such as drug testing and analytics e.g. biomimetic NFCA scaffolds for hepatic tissue constructs with different hepatic cell lines to perform for example drug screening.

A wire structure analogous to the NFCA-HepG2 described above in Example 1 was coated with collagen to enable cell seeding on the surface of the wire. The collagen working solution was prepared from type I collagen stock solution (Rat Collagen I (LV) 3 mg/ml, Cultrex) according to the manufacturer's guidelines with the exception that DMEM was used instead of water to dilute the stock solution. The concentration of type I collagen in the working solution was 1 mg/ml.

The collagen working solution was pipetted upon the newly produced wire structure. The wires were soaked in collagen working solution and placed into a cell culture incubator for 30 minutes to allow collagen gel formation. After incubation the wires were transferred to 6-well plates for SK-HEP-1 cell seeding. SK-HEP-1 cells were detached, suspended and introduced with the collagen coated NFCA-HepG2 wires. Cell seeding was performed on non-treated culture plates for non-adhering cells. During a 2 hour period the well plates were incubated and subsequently shaken every 30 minutes to allow SK-HEP-1 cell attachment on the collagen treated wire surface. After cell seeding, the well plates were placed into 37° C. in 5% $CO_2$ and incubated from 48 hours up till 2 weeks until confocal imaging.

NFCA-wires coated with type I collagen are presented in FIGS. 3a, 3b, 4a, 4b, 5b, 6a and 6b.

Example 3

Coating of Surgical Sutures With NFCA-Cell Composition

NFCA-cell compositions were used to produce coatings. The crosslinking procedure resulted in the formation of the final coating. E.g. biodegradable sutures were coated in this manner to prepare medical devices for post-surgical procedures (e.g. Crohn's disease fistula treatment with mesenchymal adult stem cells or treatment of defects of oral mucosa, such as ulcers, with mesenchymal stem cells). Cells could be embedded into the suture without the need of additional injections. In Crohn's disease as well as in defects of oral mucosa the release of cells were induced with ingestion of cellulases or with cellulase enzymes already present within the surgical suture.

A biodegradable synthetic polyester surgical suture (Velosorb Fast, 3-0) was coated with a NFCA-HepG2 composition using a syringe. The surgical suture was placed so that it runs through the syringe i.e. through the syringe barrel, its mouthpiece and the needle orifice. The syringe was filled with NFCA-HepG2 composition. The NFCA-cell composition was fed through the needle by gently pushing the plunger. Simultaneously the surgical suture was pulled at a rate that ensured the formation of an even layer of the NFCA-cell composition on the surface of the surgical suture. Next a crosslinking procedure analogous to that described before was performed to the suture covered in NFCA-cell composition. This resulted in the formation of the final coating. Directly after the crosslinking the sutures were sewn through pig liver sections and analyzed with confocal microscopy.

Surgical sutures with NFCA-HepG2 coating are presented in FIGS. 7a, 7b, 8a, 8b and 8c.

Example 4

Methodology for Confocal Microscopy

Leica TCS SP5II HCS A confocal images taken with HC PL APO 10x/0.4 objective using Red (HeNe 633 nm/12 mW) and Lime (DPSS 561 nm/20 mW) lasers with PTM detectors. Live/Dead imaging was performed with fluorescein diacetate (FDA) and propidium iodide (PI) cellular stains (Molecular Probes®, USA) for live and dead cells respectively. Cell co-culture imaging was carried out with dyes CellTracker™ Green CMFDA and Red CMTPX (Molecular Probes®, USA) for HepG2 and SK-HEP-1 cells respectively.

Example 5

NFCA Cell Studies

NFCA wires were seeded with HepG2 cells and incubated for up to 2 weeks. Confocal microscopy images show good cell viability within the NFCA wires with a few dead cells in both 1 week (FIG. 1 a-c) and 2 week (FIG. 1 d) incubation times.

Figure 2:
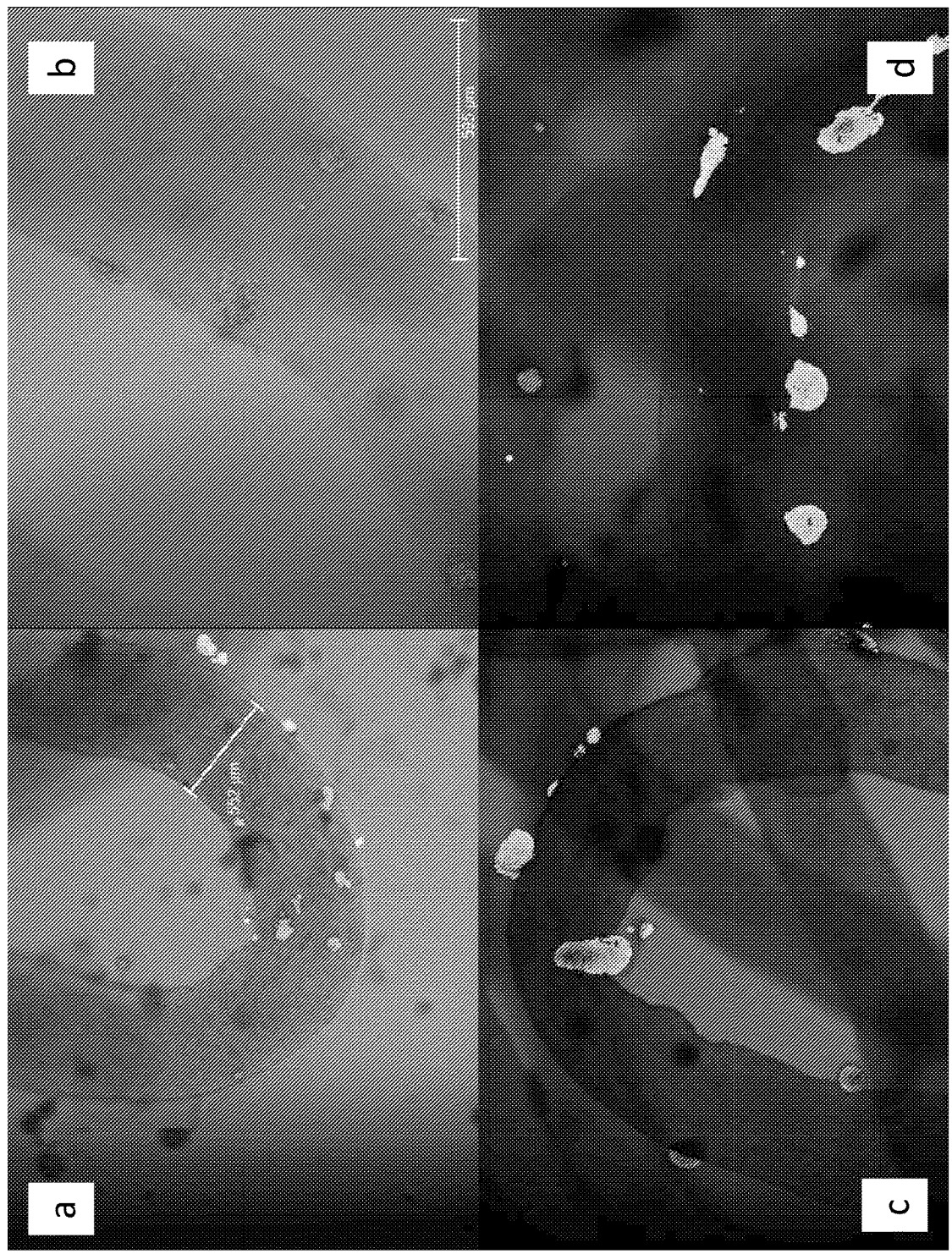
FIG. 2a depicts Type-I collagen coated NFCA wire. HepG2 cells incubated with NFCA wire coated with type-I collagen (3.26 mg/ml, 5+25 mins incubation, RT). Image after 1 week of incubation. Scale bar 552 μm.
FIG. 2b depicts Type-I collagen coated NFCA wire. HepG2 cells incubated with NFCA wire coated with type-I collagen (3.26 mg/ml, 5+25 mins incubation, RT). Image after 1 week of incubation. Cells killed with EtOH (control for dead cells in live (FDA)/dead(PI) staining). Scale bar 595 μm.
FIG. 2c depicts Type-I collagen coated NFCA wire. HepG2 cells incubated with NFCA wire coated with type-I collagen (3.26 mg/ml, 5+25 mins incubation, RT). Image after 2 weeks of incubation.
FIG. 2d depicts Type-I collagen coated NFCA wire. HepG2 cells incubated with NFCA wire coated with type-I collagen (3.26 mg/ml, 5+25 mins incubation, RT). Image after 2 weeks of incubation.

No dead cells were found in collagen coated NFCA wires when cells were seeded on the surface of the wire (FIG. 2). Very different growing properties were found depending on the seeding site. HepG2 cells on the surface showed a typical cluster like growth and hepatic morphology; however cells seeded within the wire were observed to grow individually or only in small clusters. Dead cell staining was confirmed by killing the culture with 70% ethanol treatment before confocal microscopy showing a 100% rate for dead cells (FIG. 2b).

Figure 3:
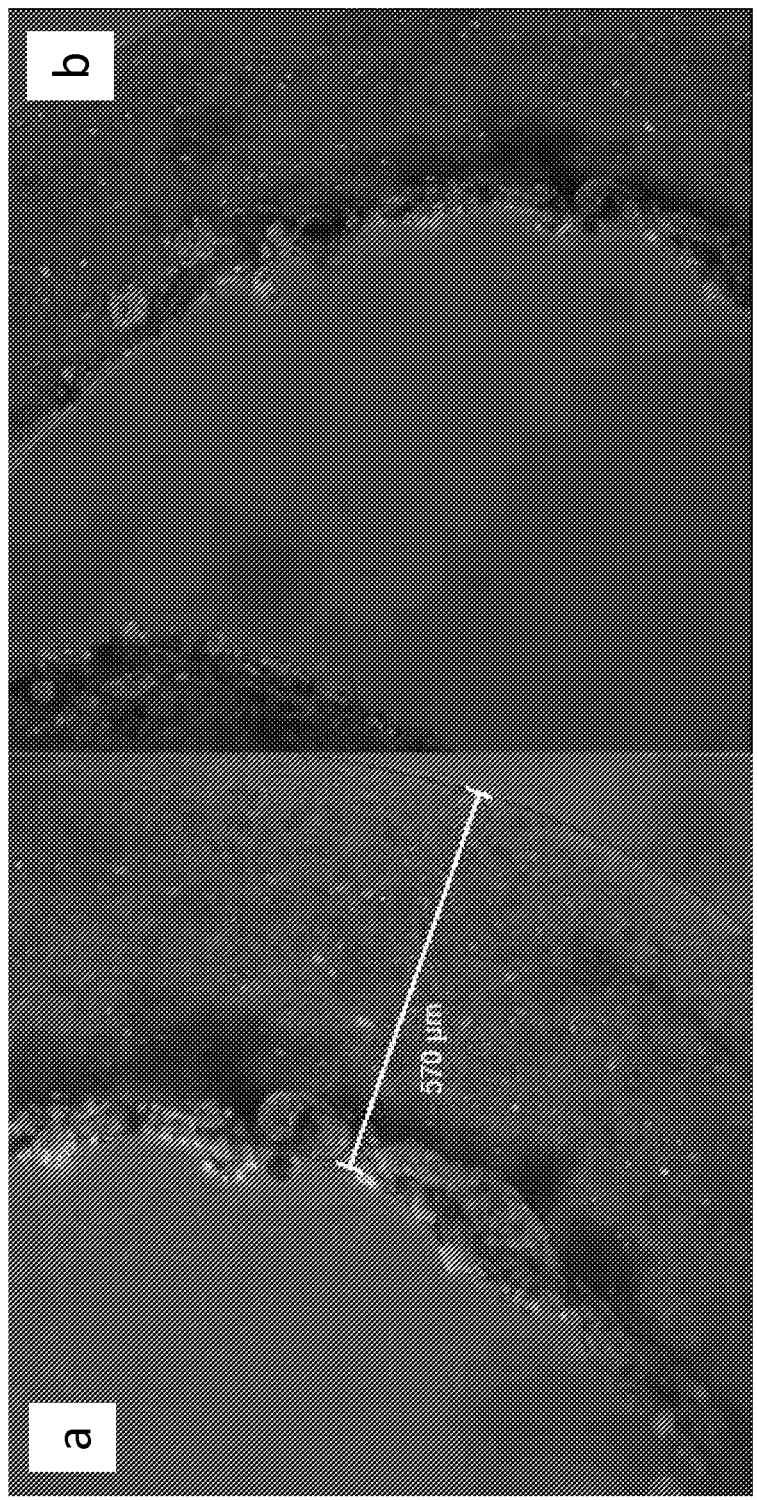
FIG. 3a depicts Type-I collagen coated NFCA-HepG2 wire (HepG2). HepG2 cells stained with CTred and CTgreen. Type-I collagen coated NFCA-HepG2 wire (1 mg/ml, 30 min incubation, 37° C.). HepG2 cells were seeded on the surface of collagen coated wire and incubated for 72 h. Note: collagen coating was unevenly distributed.
FIG. 3b depicts Type-I collagen coated NFCA-HepG2 wire (HepG2). HepG2 cells stained with CTred and CTgreen. Type-I collagen coated NFCA-HepG2 wire (1 mg/ml, 30 min incubation, 37° C.). HepG2 cells were seeded on the surface of collagen coated wire and incubated for 72 h. Note: collagen coating was unevenly distributed.

Cell co-culture properties of NFCA wires were investigated. HepG2 cells were seeded within and on the surface of the wires and incubated for 72 hours (FIGS. 3a and b). Similarly to the previous findings, cells within the wire grew individually or in small clusters containing only a few cells. Cells on the surface showed strong hepatic type growth typical to the HepG2 cell line.

Figure 4:
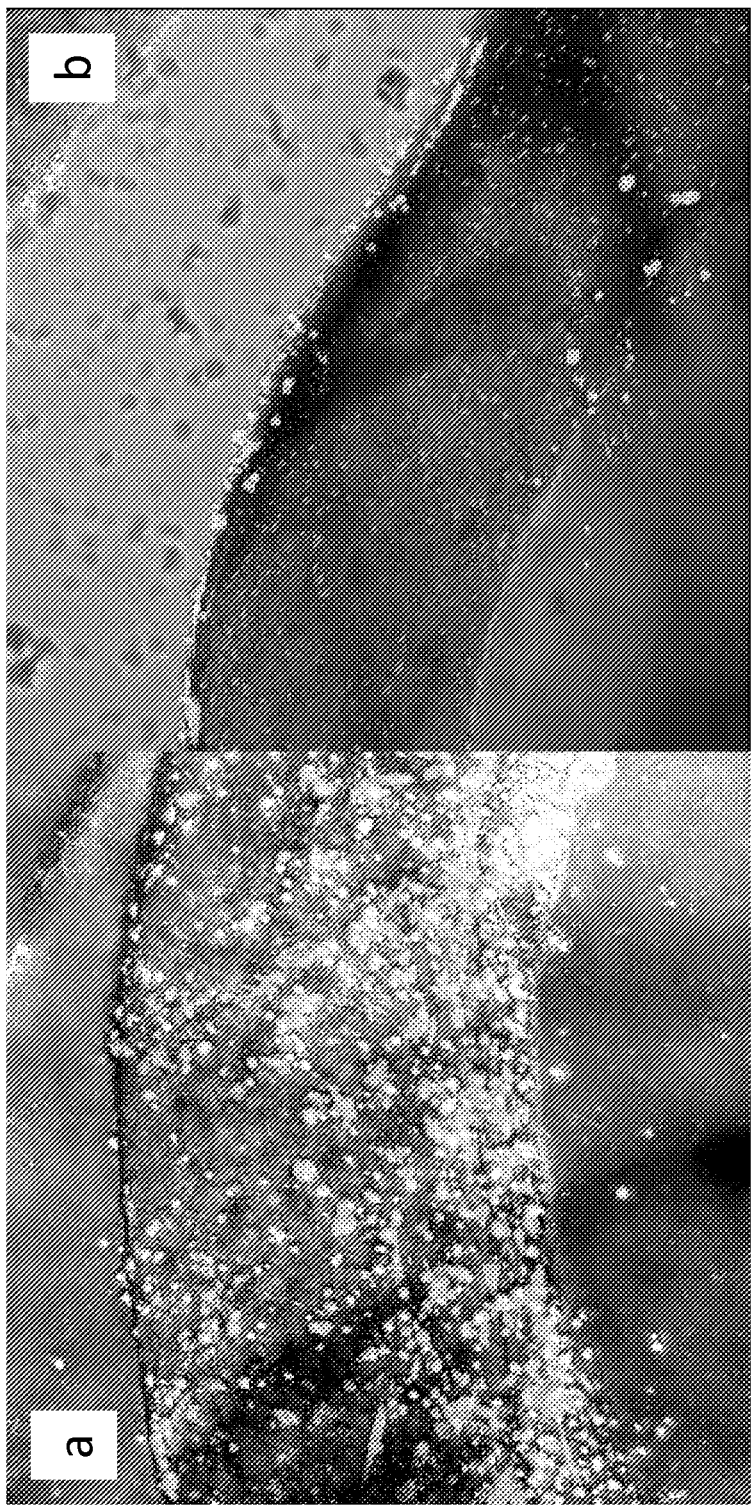
FIG. 4a depicts Type-I collagen coated NFCA-HepG2 wire (SK-HEP-1). HepG2 cells stained with CTred and SK-HEP-1 cells with CTgreen. Type-I collagen coated NFCA-HepG2 wire (1 mg/ml, 30 min incubation, 37° C.). SK-HEP-1 cells were seeded on the surface of collagen coated wire and incubated for 48 h. Note: collagen coating was unevenly distributed; however with successful coating the formation of SK-HEP-1 endothelia can be observed.
FIG. 4b depicts Type-I collagen coated NFCA-HepG2 wire (SK-HEP-1). HepG2 cells stained with CTred and SK-HEP-1 cells with CTgreen. Type-I collagen coated NFCA-HepG2 wire (1 mg/ml, 30 min incubation, 37° C.). SK-HEP-1 cells were seeded on the surface of collagen coated wire and incubated for 48 h. Note: collagen coating was unevenly distributed; however with successful coating the formation of SK-HEP-1 endothelia can be observed.

Another cell line was chosen to investigate the NFCA wire co-culture surface growth properties. SK-HEP-1 cells were seeded on top of the NFCA surface additionally to the HepG2 cells within the wire and incubated for 48 hours. As opposed to the cluster like HepG2 morphology, SK-HEP-1 cell growth showed the beginning of a monolayer epithelial-like morphology which is typical to the endothelial cell line (FIG. 4a). However it should be noted that the collagen coating was not observed to perfectly cover the wire, and either SK-HEP-1 or HepG2 did not grow on top of bare NFCA.

Example 6

NFCA Coated Surgical Sutures

Figure 5:
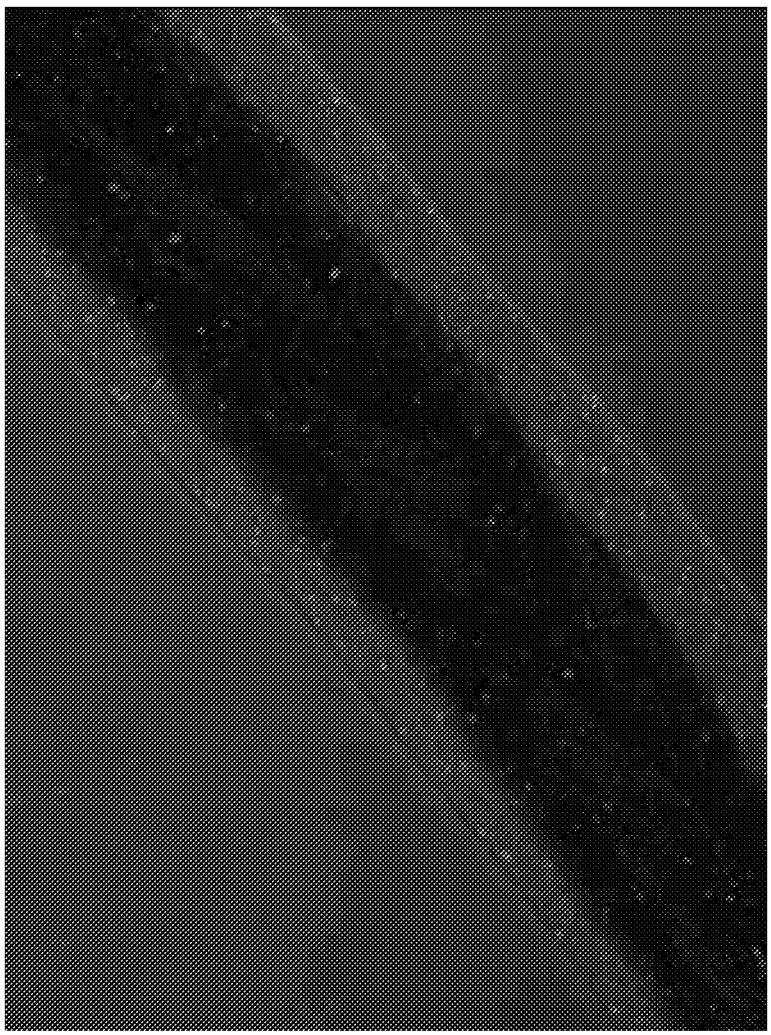
FIG. 5 depicts surgical sutures with NFCA-HepG2 coating. Stained with CTred, 72 h incubation.

HepG2 cells were seeded within the NFCA composition, extruded through a syringe needle as a layer on top of standard absorbable surgical sutures and incubated for 72 hours. HepG2 growth was shown, as previously observed, small clusters or as individual cells (FIG. 5). NFCA-HepG2 coating was shown mostly even on top of the suture; however some inconsistencies were found where the coating was not evenly distributed. The extruding force seemed to impact more on the coating thickness than the needle gauge (data not shown).

Figure 6:
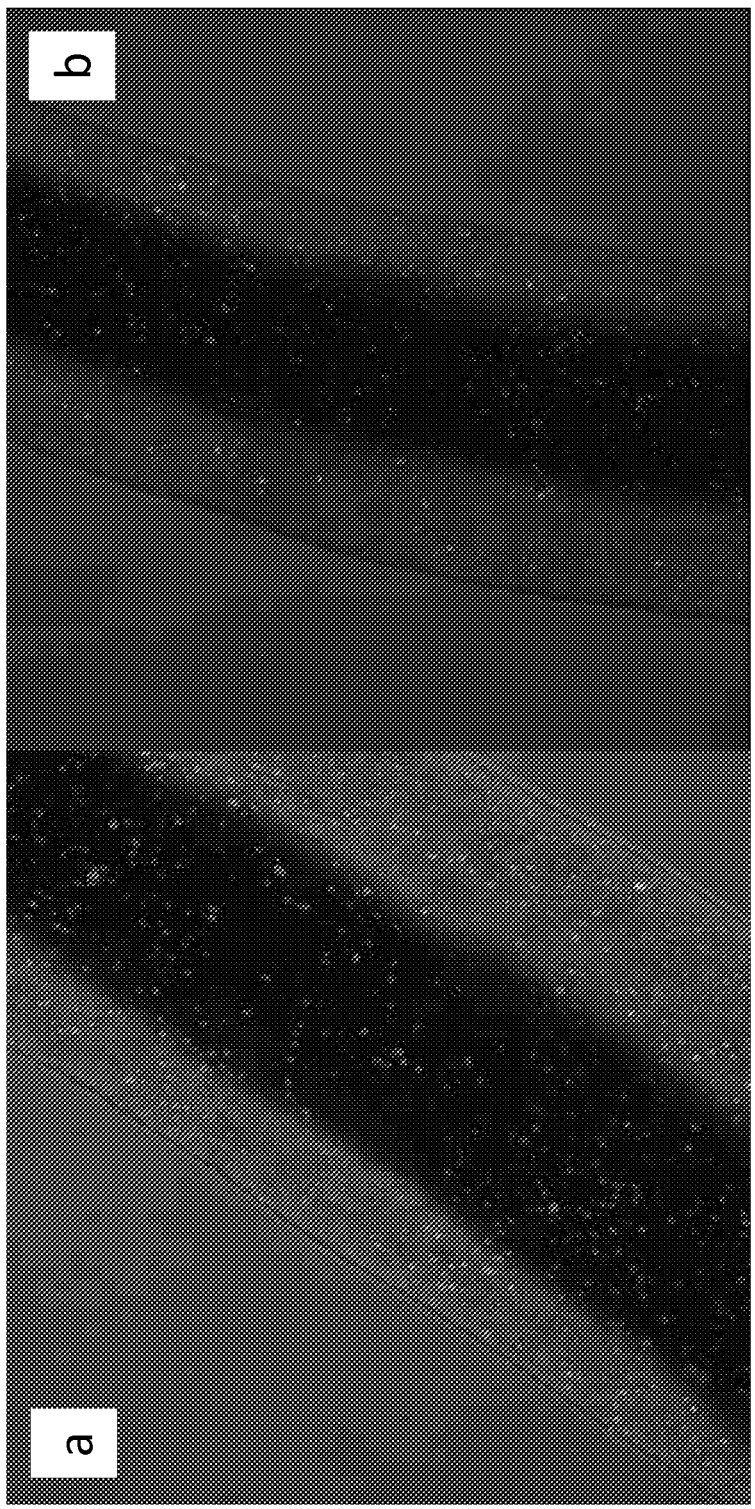
FIG. 6a depicts surgical sutures with NFCA-HepG2 coating. Stained with CTred, 72 h incubation.
FIG. 6b depicts surgical sutures with NFCA-HepG2 coating. Stained with CTred. Simulated soft tissue suture was done directly after crosslinking. Wire was sewn once through a pig liver section.
Figure 7:
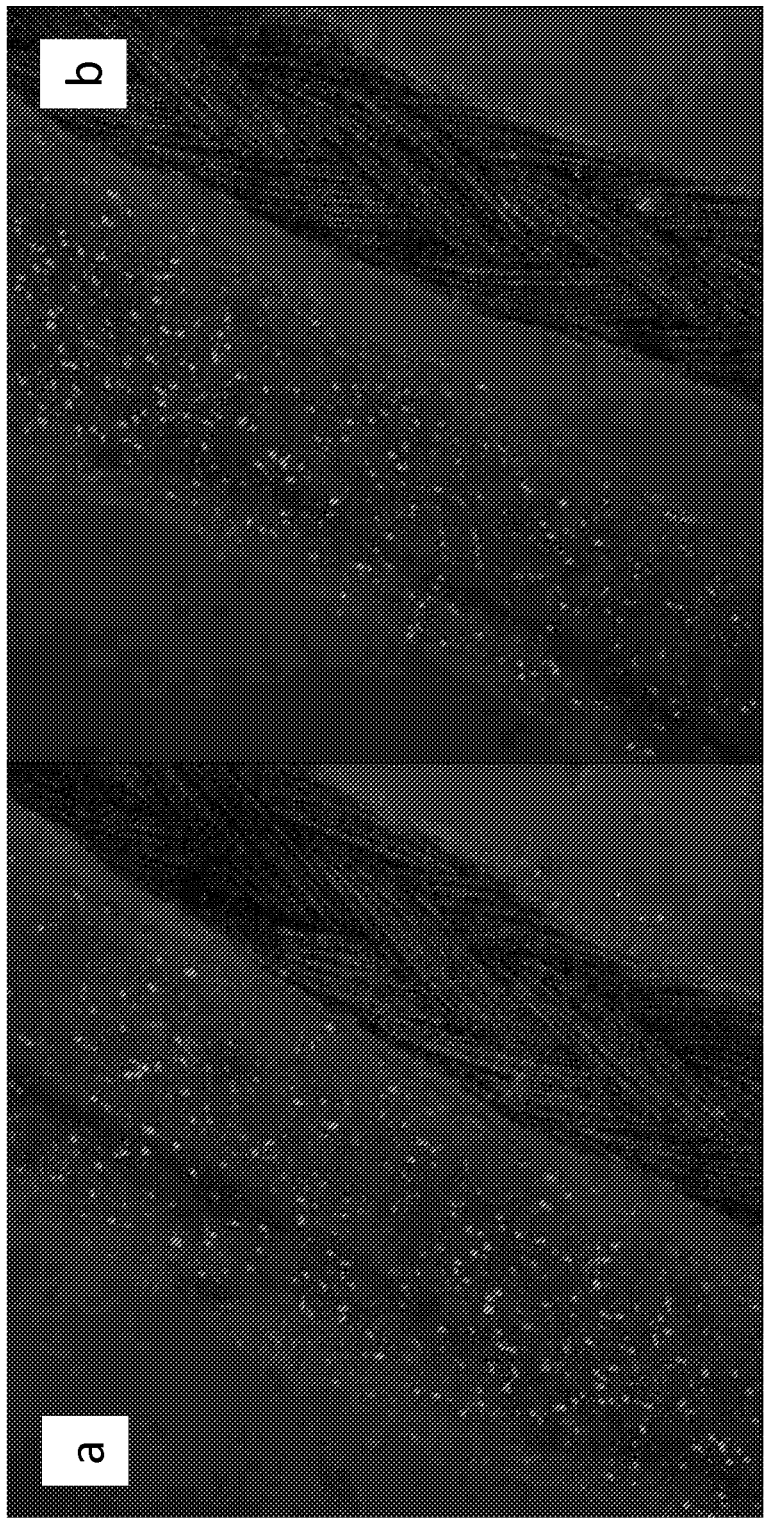
FIGS. 7a and b depicts surgical sutures with NFCA-HepG2 coating. Surgical sutures coated with NFCA-HepG2. Stained with CTred. Simulated soft tissue suture was done directly after crosslinking. Wire was sewn once through a pig liver section.

The NFCA-HepG2 coated sutures were used to simulate sewing through small pig liver segments. The coating remained intact on top of the suture wire after it was sewn through the liver segment a few times (FIGS. 6a and b). The NFCA-HepG2 coating could be easily removed from the suture as long segments without it breaking apart (FIGS. 7a and b).

Example 7

NFCA Wire Rheological Properties

Figure 8:
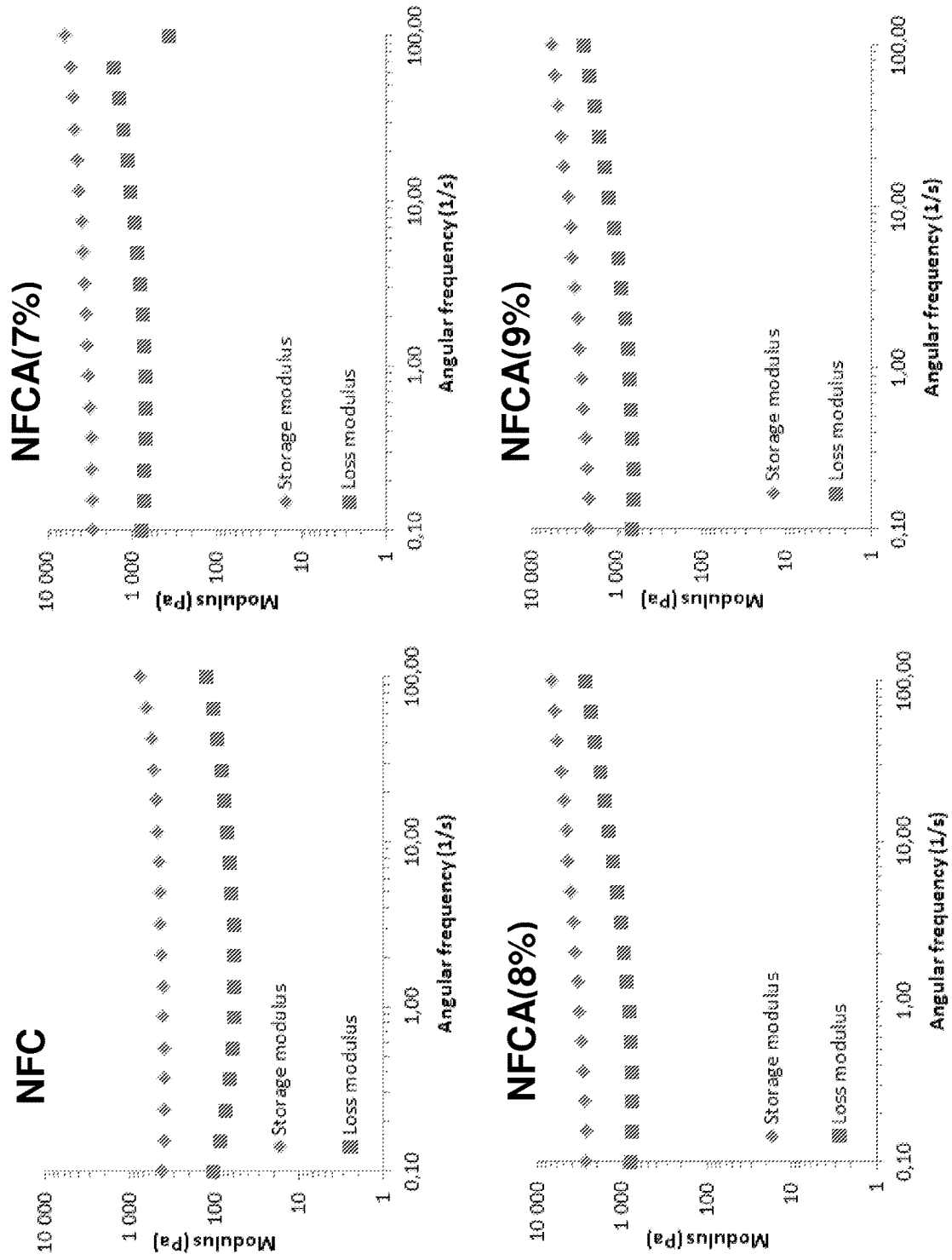
FIG. 8 depicts Frequency sweeps of crosslinked NFCA samples. NFC network shows increased strength with the addition of alginate.

The prepared NFCA wires were strong enough to withstand handling during the cell studies and surgical suture coating experiment with simulated soft tissue sutures in pig liver segments. However, rheological measurements were conducted to see how sodium alginate content, divalent salt treatment, and adding cells and culture media affect the properties of the gels. Viscosity is an important property that affects the printability of the gels, and storage and loss moduli affect the behavior of the cells that are cultured in the gels. Results of the frequency sweep measurements: storage and loss moduli of the samples were plotted as a function of the angular frequency (FIG. 8). The storage moduli are greater than loss moduli for all samples, and the loss tangent is 0.17 for NFC and close to 0.3 for other samples. This suggests that the network structure of the hydrogels is elastic. NFCA samples show higher storage and loss moduli values, strengthening the NFC network (Table 2).

TABLE 2

Viscoelastic properties of the hydrogel samples: Storage modulus (G'), loss modulus (G"), loss tangent (tan__), steady state viscosity (__) and critical shear stress (__).

|  | G' (Pa) | G" (Pa) | tan δ | μ (Pas) | τ (Pa) |
|---|---|---|---|---|---|
| NFC | 480 | 80 | 0.17 | 36 000 | 50 |
| NFC + Z7% | 4 200 | 1 200 | 0.29 | 148 000 | 150 |
| NFC + Z8% | 5 600 | 1 800 | 0.32 | 194 000 | 170 |
| NFC + Z9% | 4 900 | 1 600 | 0.33 | 385 000 | 200 |
| NFC + Z7% X | 4 000 | 900 | 0.23 | 265 000 | 170 |
| NFC + Z8% X | 4 200 | 1 300 | 0.31 | 312 000 | 200 |
| NFC + Z9% X | 3 500 | 1 100 | 0.31 | 316 000 | 210 |
| NFC + Z8% + C | 1 100 | 600 | 0.54 | 38 000 | 70 |
| NFC + Z8% + M | 1 200 | 700 | 0.58 | 18 000 | 60 |

Figure 9:
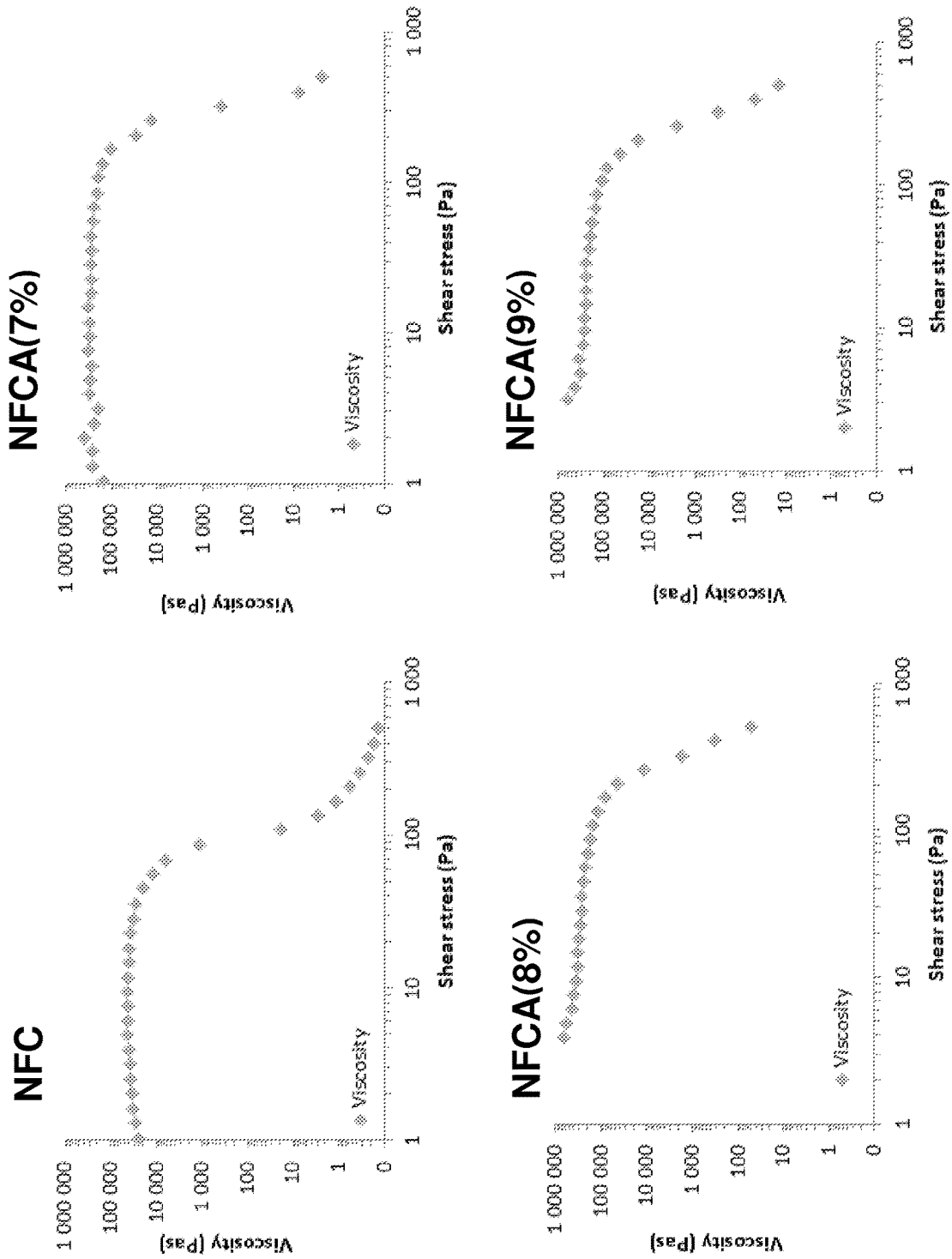
FIG. 9 depicts Shear stress sweeps of NFC and NFCA cross-linked samples. Addition of alginate increases viscosity and critical shear stress.

The viscosity in the steady state (low shear stress) increases significantly, in addition to the stress threshold for shear thinning, when sodium alginate is added (FIG. 9). Salt-treatment (i.e. crosslinking) slightly increased those values further. There is also visible change in the shape of the curves when sodium alginate is present: the viscosity of NFC drops quite clearly around 80 Pa, but the shear thinning of other samples happens over a broader range of stress. In addition it seems that the thinning continues beyond the 500 Pa range used in these experiments. This is most likely due to the difference in the shear thinning properties of NFC and alginate.

Example 8

NFCA Wire Sutures on Small Animal Tissue

Freshly sacrificed BALB/c mice and a Wistar rat were used to evaluate the performance of the surgical sutures coated with NFCA. Sutures were coated with NFCA and crosslinked in similar fashion as described above. Target soft tissue was sutured and instrument ties were performed to complete the sutures. Mouse liver, spleen, intestine, muscle and skin in addition to rat intestine, testis and skin were selected for the performance test.

Figure 10:
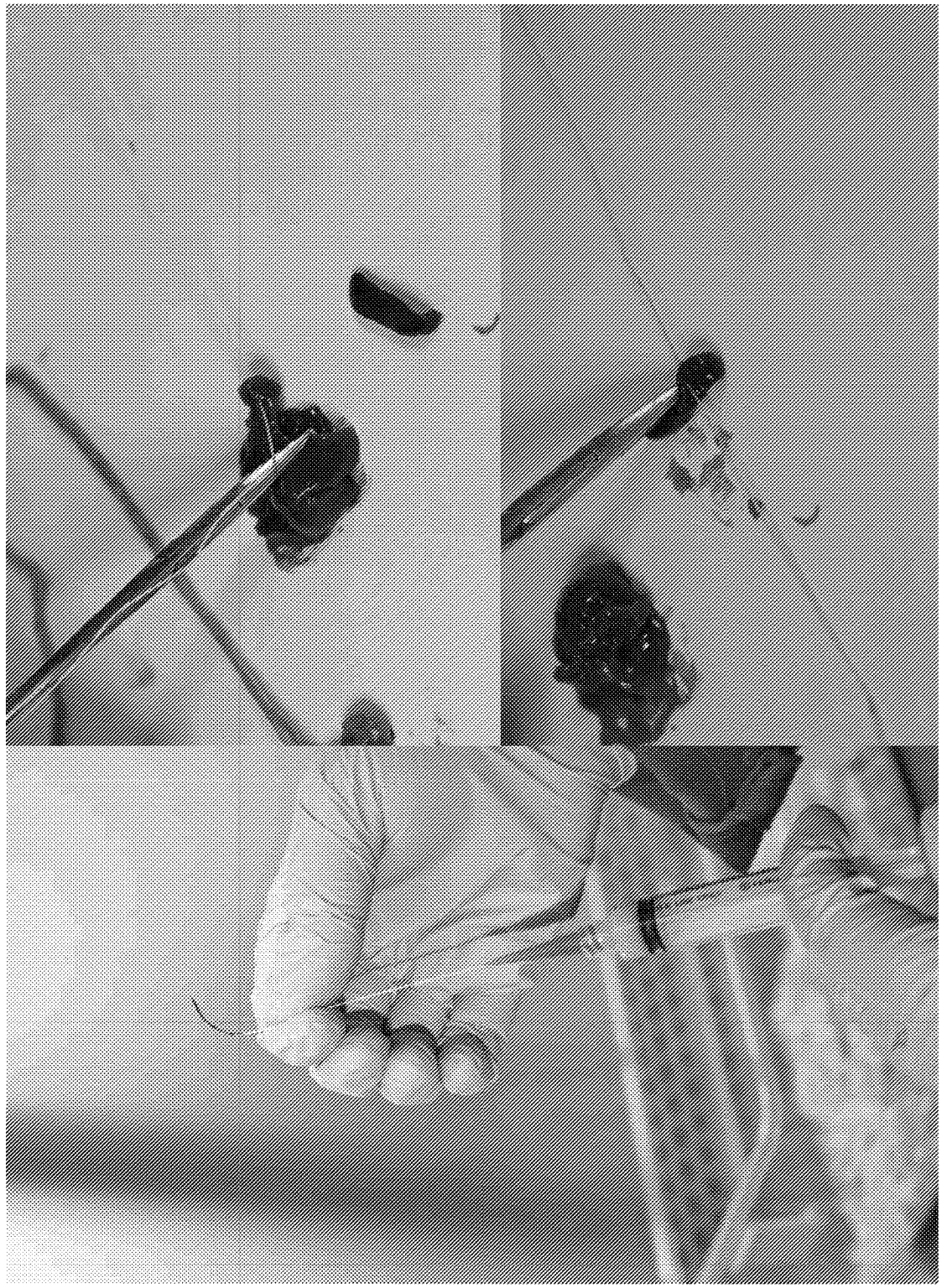
FIG. 10 depicts NFCA coating preparation method and performance testing of surgical sutures on mouse liver and spleen. NFCA coated sutures were prepared (left) and were tested on small animal internal organs: mouse liver (top) and spleen (bottom). Sutures handled well; however felt slightly rigid due to the crosslinking process.
Figure 11:
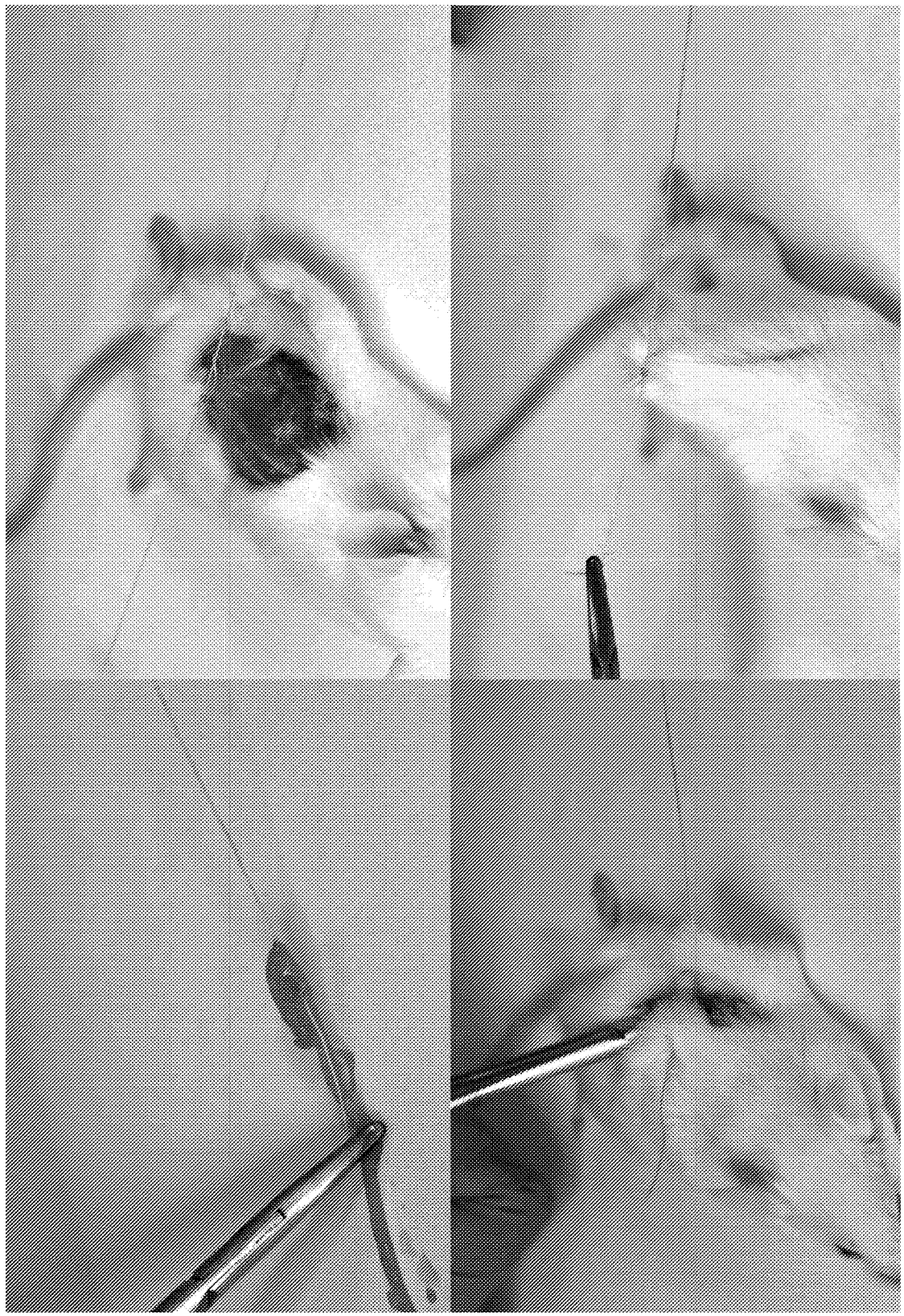
FIG. 11 depicts NFCA coated sutures and performance testing on mouse intestine (top left), muscle tissue (top right) and skin (bottom). Muscle and skin were sutured with instrument method ties. Coating remained intact during the suturing process.

NFCA coating of standard absorbable surgical sutures were performed as described above. Sutures were crosslinked with $Ca^{2+}$ and $Ba^{2+}$ before attempting to suture various internal organs and tissue of freshly sacrificed mice and a rat. Performance testing showed slightly rigid behavior of the suture; however the overall handling felt comfortable. Mouse soft tissue: spleen and liver (FIG. 10) in addition to intestine, muscle tissue and skin (FIG. 11) were sutured successfully. Instrument knots were performed to complete the sutures on muscle tissue and skin without complications.

Figure 12:
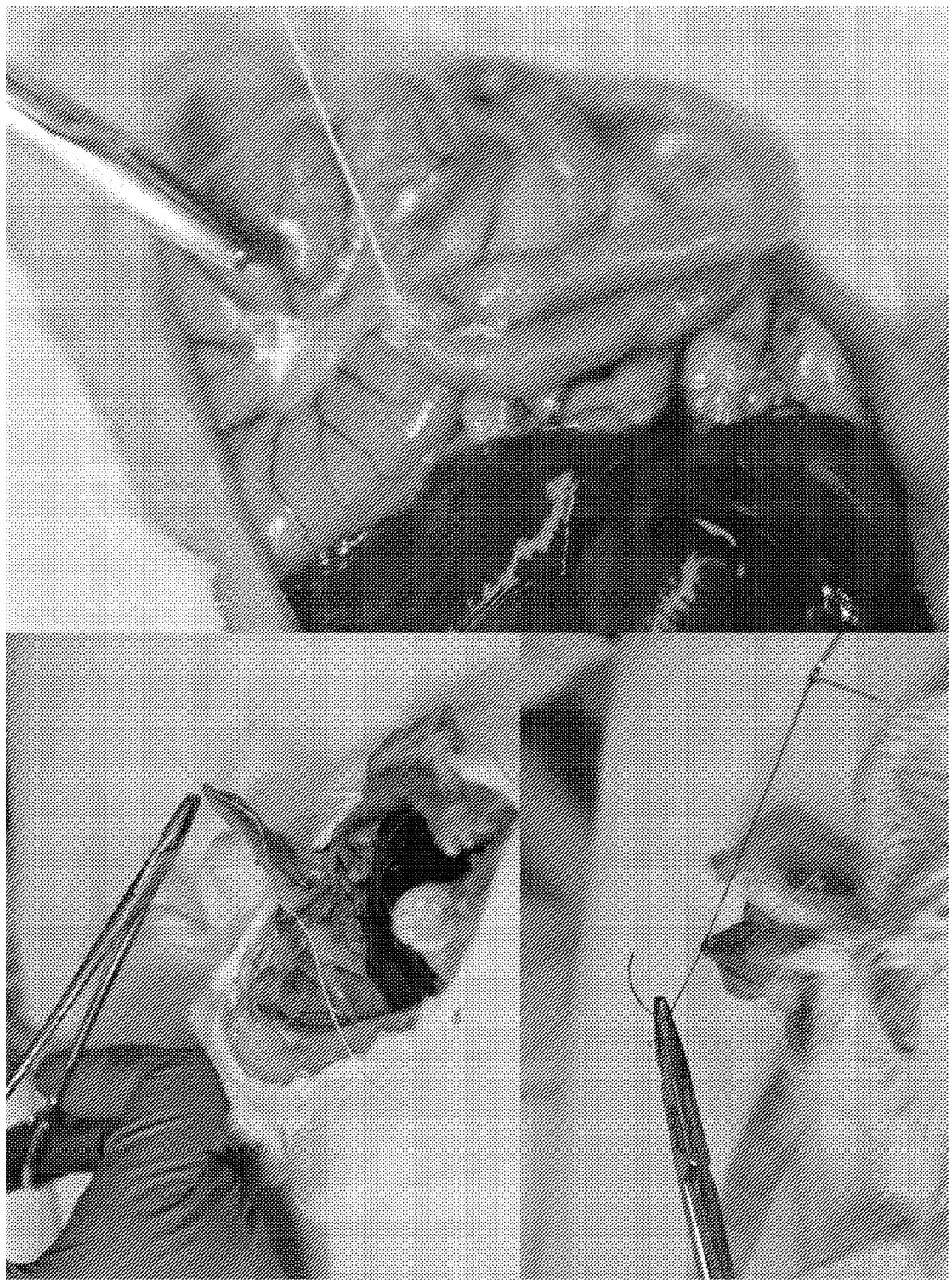
FIG. 12 depicts NFCA coated sutures and performance testing on rat intestine (top left) and testis (bottom left). The suture on rat intestine showed peeling off of the NFCA coating (highlighted by the arrow; right). Peeling off is probably due to manual preparation of NFCA coated sutures; therefore causing imperfect formation of fully intact coating. However, the failed sutures are clearly visible and easily noticed.
Figure 13:
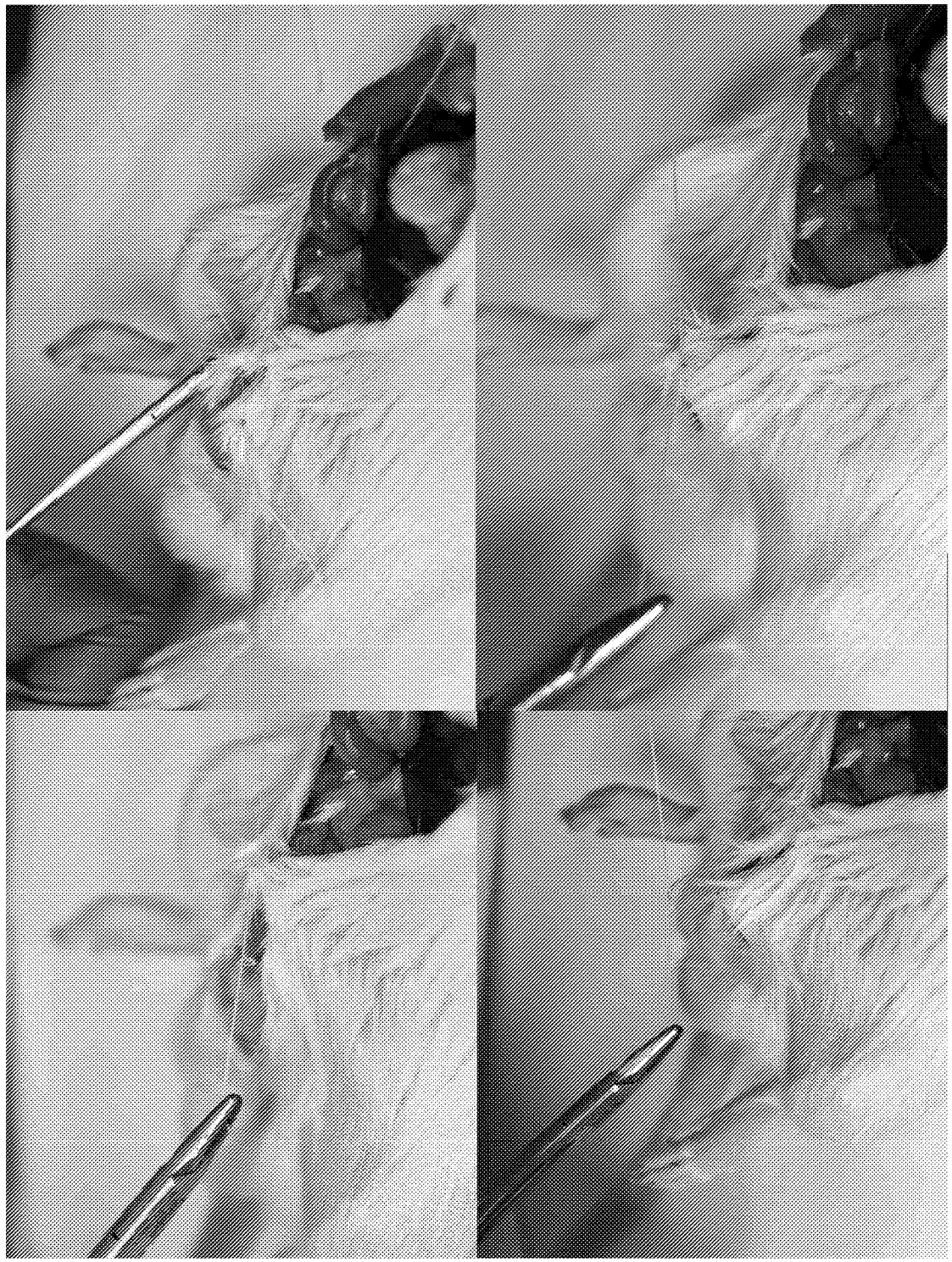
FIG. 13 depicts NFCA coated sutures and performance testing on rat skin. In addition to rat intestine, successful suture on rat skin is shown on top right, some peeling off was observed also on the skin (highlighted by the arrow; top left). However, the second suture and knot tying was performed successfully without the coating peeling off (bottom). The manual preparation method was not shown entirely reliable; however most sutures were successful and handled well in the process.

Rat intestine and skin showed slight peeling off of the NFCA coating (FIG. 12, 13). Peeling off was shown clearly in the tissue and sutures, indicating that the manual preparation method was not entirely reliable. However, most attempts were successful and knot tying was performed on rat skin without peeling off (FIG. 12). Sutures performed well with some complications on rat intestine and skin and no complications on mice. Peeling off was observed in previous confocal images and therefore was not entirely unexpected. The rate of successfully coated sutures could be potentially improved with better preparation methods.

REFERENCES

Andersen T. et al. Ionically gelled alginate foams: physical properties controlled by operational and macromolecular parameters. Biomacromolecules. 12:13(11):3703-10, 2012.

Falanga V. Stem Cells in Tissue Repair and Regeneration. J Invest Dermatol 132: 1538-1541, 2012.

Kuo C. K. and Ma P. X. Ionically crosslinked alginate hydrogels as scaffolds for tissue engineering: part 1. Structure, gelation rate and mechanical properties. Biomaterials 22(6):511-521, 2001.

Kuthcarlapati et al. Metals Materials and Processes 20(3): 307-314, 2008.

Ma Y. and Coombes A. G. Designing colon-specific delivery systems for anticancer drug-loaded nanoparticles: an evaluation of alginate carriers. J Biomed Mater Res A. 102(9):3167-3176, 2014.

Mansour H. M. et al. Materials for Pharmaceutical Dosage Forms: Molecular Pharmaceutics and Controlled Release Drug Delivery Aspects. Int. J. Mol. Sci. 11:3298-3322, 2010.

Sirviö J. A. et al. Biocomposite cellulose-alginate films: Promising packaging materials. Food Chemistry 151:343-351, 2014.

Wu Y. et al. Mesenchymal Stem Cells Enhance Wound Healing Through Differentiation and Angiogenesis. Stem Cells 25:2648-2659, 2007.

Yoo S. M. et al. Fabrication of alginate fibers using a microporous membrane based molding technique. Biochem Eng J 91:58-65, 2014.

The invention claimed is:

1. A composition comprising:
    nanofibrillar cellulose;
    a cross-linkable polymer;
    cross-linking cations including $Ca^{2+}$ and $Ba^{2+}$ in a ratio selected from about 1:1 to about 4:1; and
    at least one bioactive agent,
    wherein the composition is a matrix.

2. A method for preparing the composition according to claim 1, the method comprising:
    combining, in any order, the nanofibrillar cellulose, the cross-linkable polymer, the cross-linking cations, and the at least one bioactive agent.

3. The method according to claim 2, the method further comprising cross-linking said cross-linkable polymer by exposing the composition to cross-linking conditions or chemicals.

4. The method according to claim 3, further comprising shaping the composition, optionally in or on a secondary material with concomitant or subsequent cross-linking.

5. The method according to claim 2, wherein the nanofibrillar cellulose is in the form of a hydrogel, the combining step comprises mixing the at least one bioactive agent into the nanofibrillar cellulose hydrogel, optionally followed by incubation, and adding the cross-linkable polymer to the composition.

6. The method according to claim 2, wherein the nanofibrillar cellulose is in the form of a hydrogel, the combining comprises mixing the cross-linkable polymer into the nanofibrillar cellulose hydrogel, and mixing the at least one bioactive agent therein, optionally followed by incubation.

7. The composition according to claim 1, wherein the matrix is a shaped matrix.

8. The composition according to claim 7, wherein the shaped matrix is a wire, a cord, a tube, a mesh, a bead, a sheet, a web, a coating, an interlayer, or an impregnate.

9. The composition according to claim 1, wherein the matrix comprises semi interpenetrated polymer networks (semi-IPN) of nanofibrillar cellulose and the at least one cross-linked polymer.

10. The composition according to claim 1, wherein the at least one bioactive agent is encapsulated in the matrix.

11. The composition according to claim 1, wherein the matrix is in the form of a hydrogel.

12. The composition according to claim 1 for use in therapy, surgery, or diagnostics.

13. The composition according to claim 1 for use in therapy, wherein the therapy comprises treating of Crohn's disease or oral mucosa defects.

14. The composition according to claim 1, wherein the composition is a suture coating.

15. Use of the composition according to claim 1 in biodegradable structures.

16. The composition according to claim 1, wherein the composition is a cosmetic composition.

17. A biomedical device comprising the composition according to claim 1, wherein the composition is in the form of a body or at least one layer.

18. The biomedical device according to claim 17, further comprising a planar or elongated element at least partially coated by or embedded in the matrix.

19. The biomedical device according to claim 17, wherein the matrix is a generally planar or elongated body or bodies.

20. The composition according to claim 1, wherein the nanofibrillar cellulose is a nanofibrillar cellulose dispersion.

21. The composition according to claim 1, wherein the nanofibrillar cellulose is native nanofibrillar cellulose.

22. The composition according to claim 1, wherein the nanofibrillar cellulose is plant-derived nanofibrillar cellulose.

23. The composition according to claim 1, wherein the concentration of the nanofibrillar cellulose is from 0.1% to 10% (w/w).

24. The composition according to claim 1, wherein the cross-linkable polymer is a biocompatible polymer.

25. The composition according to claim 1, wherein the cross-linkable polymer is an anionic polymer.

26. The composition according to claim 25, wherein the cross-linking cations further comprise $Mg^{2+}$.

27. The composition according to claim 26, wherein the cross-linking cations are used in an amount from 10 mM to 1000 mM.

28. The composition according to claim 1, wherein the amount of the cross-linkable polymer is from 1% to 20% (w/w).

29. The composition according to claim 1, wherein the cross-linkable polymer is alginate or alginate-like.

30. The composition according to claim 29, wherein the amount of the alginate is from 1% to 20% (w/w).

31. The composition according to claim 1, wherein the bioactive agent is selected from the group consisting of cells, drugs, drug conjugates, anti-viral compounds, antibiotic compounds, cell differentiating agents, wound repair agents, anti-proliferatives, analgesics, angiogenic agents, anti-angiogenic agents, anti-thrombotics, anti-clotting agents, clotting agents, adhesion-preventing agents, antipyretics, anaesthetics, anticonvulsants, antihistamines, anti-inflammatories, agents that act on the immune system, cardiovascular drugs, diagnostic agents, sympathomimetics, cholinomimetics, antimuscarinics, antispasmodics, hormones, growth factors, retinoids, cell adhesion factors, osteogenic factors, muscle relaxants, adrenergic antagonists, antineoplastics, immunogenic agents, immunosuppressors, immunostimulatory agents, neurotransmitters, digestive drugs, prodrugs, diuretics, steroids, lipids, narcotics, lipopolysaccharides, polysaccharides, peptides, polypeptides, proteins, carbohydrates, enzymes, viral particles, vectors, antibodies, antigens, therapeutic oligonucleotides, nucleic acids, and nucleic acid fragments, contrast agents for medical diagnostic imaging, and combinations thereof.

32. The composition according to claim 1, wherein the bioactive agent includes at least one type of cells selected from the group consisting of undifferentiated cells, precursor cells, fully differentiated cells, autologous cells, allogeneic cells, stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, cord blood cells, embryonic stem cells, induced pluripotent cells, placental cells, bone marrow derived cells, immune system cells, hematopoietic cells, dendritic cells, hair follicle cells, chondrocytes, cardiomyocytes, and hybridoma cells, and combinations thereof.

33. A method for degrading the composition according to claim 1, further comprising treating the matrix with enzymes configured to degrade nanofibrillar cellulose, and/or with enzymes capable of degrading the cross-linked polymer.

34. The composition according to claim 1, wherein the ratio is about 1:1, 2:1, 2.5:1, 2.6:1, 2.7:1, 2.8:1, 2.9:1, 3:1, 3.1:1, 3.2:1, 3.3:1, 3.4:1, 3.5:1, or 4:1.

35. The composition according to claim 1, wherein the cross-linking cations further include at least one of $Fe^{3+}$, $Al^{3+}$, or $Sr^{2+}$.

* * * * *